US006772642B2

(12) United States Patent
Hajduk et al.

(10) Patent No.: US 6,772,642 B2
(45) Date of Patent: Aug. 10, 2004

(54) HIGH THROUGHPUT MECHANICAL PROPERTY AND BULGE TESTING OF MATERIALS LIBRARIES

(76) Inventors: Damian A. Hajduk, 1146 Brace Ave., San Jose, CA (US) 95125; Eric D. Carlson, 10226 Alpine Dr., #3, Cupertino, CA (US) 95014; J. Christopher Freitag, 1110 Lincoln St., Santa Clara, CA (US) 95050; Oleg Kolosov, 1045 Arlington La., San Jose, CA (US) 95129; James R. Engstrom, 138 Campbell Ave., Ithaca, NY (US) 14850; Adam Safir, 1609 Virginia St., Berkeley, CA (US) 94703; Ravi Srinivasan, 1934 Silverwood Ave., Mountain View, CA (US) 94039; Leonid Matsiev, 6514 Bibel Ave., San Jose, CA (US) 95129

( * ) Notice: Subject to any disclaimer, the term of this patent is extended or adjusted under 35 U.S.C. 154(b) by 328 days.

(21) Appl. No.: 09/939,404

(22) Filed: Aug. 24, 2001

(65) Prior Publication Data

US 2003/0041672 A1 Mar. 6, 2003

(51) Int. Cl.[7] ................................................ G01N 3/08
(52) U.S. Cl. ............................................................ 73/819
(58) Field of Search .............................. 73/819, 150 A, 73/800, 818, 826, 827, 862.041, 862.046

(56) References Cited

U.S. PATENT DOCUMENTS

| 1,870,412 A | 8/1932 | Kennedy |
| 3,071,961 A | 1/1963 | Heigl et al. |
| 3,675,475 A | 7/1972 | Weinstein |
| 3,713,328 A | 1/1973 | Aritomi |
| 3,798,960 A | 3/1974 | Glass |
| 3,805,598 A | 4/1974 | Corcoran |
| 3,818,751 A | 6/1974 | Karper et al. |
| 3,849,874 A | 11/1974 | Jeffers |
| 3,895,513 A | 7/1975 | Richardson |
| 3,908,441 A | 9/1975 | Virloget |
| 3,933,032 A | 1/1976 | Tschoegl |
| 4,229,979 A | 10/1980 | Greenwood |

(List continued on next page.)

FOREIGN PATENT DOCUMENTS

| EP | 0 317 356 A2 | 5/1989 |
| EP | 1 158 290 A2 | 11/2001 |
| JP | 402297040 A | 12/1990 |
| TW | 457336 A | 10/2001 |
| WO | WO 96/11878 | 4/1996 |
| WO | WO 97/16699 | 5/1997 |
| WO | WO 98/15501 | 4/1998 |
| WO | WO 99/18431 | 4/1999 |
| WO | WO 00/17413 | 3/2000 |
| WO | WO 00/23921 | 4/2000 |
| WO | WO 0036410 | 6/2000 |
| WO | WO 00/40331 | 7/2000 |
| WO | WO 00/51720 | 9/2000 |
| WO | WO 00/67086 | 11/2000 |
| WO | WO 01/79949 A2 | 10/2001 |
| WO | WO 03/019150 A1 | 3/2003 |

OTHER PUBLICATIONS

International Search Report for Application Ser. No. PCT/US02/26112 dated Jan. 14, 2003.

(List continued on next page.)

Primary Examiner—Max Noori

(57) ABSTRACT

A method for high throughput mechanical property and bulge testing of materials libraries. A plurality of samples on a substrate are monitored for their response to a force from a fluid.

33 Claims, 7 Drawing Sheets

U.S. PATENT DOCUMENTS

| | | |
|---|---|---|
| 4,447,125 A | 5/1984 | Lazay et al. |
| 4,517,830 A | 5/1985 | Gunn, deceased et al. |
| 4,567,774 A | 2/1986 | Manahan et al. |
| 4,570,478 A | 2/1986 | Soong |
| 4,599,219 A | 7/1986 | Cooper et al. |
| 4,602,501 A | 7/1986 | Hirata |
| 4,605,589 A | 8/1986 | Orphanides |
| 4,680,958 A | 7/1987 | Ruelle et al. |
| 4,685,328 A | 8/1987 | Huebner et al. |
| 4,699,000 A | 10/1987 | Lashmore et al. |
| 4,715,007 A | 12/1987 | Fujita et al. |
| 4,740,078 A | 4/1988 | Daendliker et al. |
| 4,749,854 A | 6/1988 | Martens |
| 4,789,236 A | 12/1988 | Hodor et al. |
| 4,793,174 A | 12/1988 | Yau |
| 4,829,837 A | 5/1989 | Telfer |
| 4,893,500 A | 1/1990 | Fink-Jensen |
| 4,899,575 A | 2/1990 | Chu et al. |
| 4,899,581 A | 2/1990 | Allen et al. |
| 4,932,270 A | 6/1990 | Lurie et al. |
| 4,975,320 A | 12/1990 | Goldstein et al. |
| 5,008,081 A | 4/1991 | Blau et al. |
| 5,051,239 A | 9/1991 | von der Goltz |
| 5,092,179 A | 3/1992 | Ferguson |
| 5,103,557 A | 4/1992 | Leedy |
| 5,115,669 A | 5/1992 | Fuller et al. |
| 5,142,900 A | 9/1992 | Duke |
| 5,193,383 A | 3/1993 | Burnham et al. |
| 5,236,998 A | 8/1993 | Lundeen et al. |
| 5,269,190 A | 12/1993 | Kramer et al. |
| 5,271,266 A | 12/1993 | Eschbach |
| 5,272,912 A | 12/1993 | Katsuzaki |
| 5,280,717 A | 1/1994 | Hoseney et al. |
| 5,303,030 A | 4/1994 | Abraham et al. |
| 5,305,633 A | 4/1994 | Weissenbacher et al. |
| 5,398,885 A | 3/1995 | Andersson et al. |
| 5,437,192 A | 8/1995 | Kawamoto et al. |
| 5,438,863 A | 8/1995 | Johnson |
| 5,452,614 A | 9/1995 | Kato et al. |
| 5,452,619 A | 9/1995 | Kawanabe et al. |
| 5,481,153 A | 1/1996 | Turner |
| 5,517,860 A | 5/1996 | Lin et al. |
| 5,520,042 A | 5/1996 | Garritano et al. |
| 5,532,942 A | 7/1996 | Kitamura et al. |
| 5,610,325 A | 3/1997 | Rajagopal et al. |
| 5,626,779 A | 5/1997 | Okada |
| 5,699,159 A | 12/1997 | Mason |
| 5,700,953 A | 12/1997 | Hlady et al. |
| 5,723,792 A | 3/1998 | Miyazaki |
| 5,728,532 A | 3/1998 | Ackley |
| 5,756,883 A | 5/1998 | Forbes |
| 5,764,068 A | 6/1998 | Katz et al. |
| 5,776,359 A | 7/1998 | Schultz et al. |
| 5,817,947 A | 10/1998 | Bergerus |
| 5,821,407 A | 10/1998 | Sekiguchi et al. |
| 5,847,283 A | 12/1998 | Finot et al. |
| 5,877,428 A | 3/1999 | Scolton |
| 5,892,157 A | 4/1999 | Syre |
| 5,922,967 A | 7/1999 | Motoyama |
| 5,959,297 A | 9/1999 | Weinberg et al. |
| 5,985,356 A | 11/1999 | Schultz et al. |
| 5,999,887 A | 12/1999 | Giannakopoulos et al. |
| 6,004,617 A | 12/1999 | Schultz et al. |
| 6,010,616 A | 1/2000 | Lewis et al. |
| 6,013,199 A | 1/2000 | McFarland et al. |
| 6,030,917 A | 2/2000 | Weinberg et al. |
| 6,033,913 A | 3/2000 | Morozov et al. |
| 6,034,240 A | 3/2000 | La Pointe |
| 6,034,775 A | 3/2000 | McFarland et al. |
| 6,040,193 A | 3/2000 | Winkler et al. |
| 6,043,317 A | 3/2000 | Mumick et al. |
| 6,043,363 A | 3/2000 | LaPointe et al. |
| 6,045,671 A | 4/2000 | Wu et al. |
| 6,050,138 A * | 4/2000 | Lynch et al. ............. 73/150 A |
| 6,050,139 A | 4/2000 | Bousfield et al. |
| 6,087,181 A | 7/2000 | Cong |
| 6,092,414 A | 7/2000 | Newman |
| 6,124,476 A | 9/2000 | Guram et al. |
| 6,149,882 A | 11/2000 | Guan et al. |
| 6,151,123 A | 11/2000 | Nielsen |
| 6,157,449 A | 12/2000 | Hajduk |
| 6,167,748 B1 | 1/2001 | Britton, Jr. et al. |
| 6,175,409 B1 | 1/2001 | Nielsen et al. |
| 6,177,528 B1 | 1/2001 | LaPointe et al. |
| 6,182,499 B1 | 2/2001 | McFarland et al. |
| 6,187,164 B1 | 2/2001 | Warren et al. |
| 6,203,726 B1 | 3/2001 | Danielson et al. |
| 6,204,656 B1 | 3/2001 | Cheiky-Zelina et al. |
| 6,225,487 B1 | 5/2001 | Guram |
| 6,225,550 B1 | 5/2001 | Hornbostel et al. |
| 6,242,623 B1 | 6/2001 | Boussie et al. |
| 6,248,540 B1 | 6/2001 | Weinberg et al. |
| 6,260,407 B1 | 7/2001 | Petro et al. |
| 6,265,226 B1 | 7/2001 | Petro et al. |
| 6,265,601 B1 | 7/2001 | Guram et al. |
| 6,267,011 B1 | 7/2001 | Kurtz et al. |
| 6,268,513 B1 | 7/2001 | Guram et al. |
| 6,294,388 B1 | 9/2001 | Petro |
| 6,296,771 B1 | 10/2001 | Miroslav |
| 6,306,658 B1 | 10/2001 | Turner et al. |
| 6,315,923 B1 | 11/2001 | Devenney et al. |
| 6,321,594 B1 | 11/2001 | Brown et al. |
| 6,326,090 B1 | 12/2001 | Schultz et al. |
| 6,336,353 B2 | 1/2002 | Matsiev et al. |
| 6,346,290 B1 * | 2/2002 | Schultz et al. ................. 427/8 |
| 6,406,608 B1 * | 6/2002 | Uzoh et al. ................. 205/101 |
| 6,438,497 B1 | 8/2002 | Mansky et al. |
| 6,489,776 B1 | 12/2002 | Stowe et al. |
| 6,507,197 B1 | 1/2003 | Itoh et al. |
| 6,564,947 B2 * | 5/2003 | Bakula ...................... 210/388 |
| 2003/0041671 A1 * | 3/2003 | Hajduk et al. ................ 73/800 |
| 2003/0041676 A1 * | 3/2003 | Hajduk et al. ......... 73/862.041 |

OTHER PUBLICATIONS

U.S. Application Ser. No. 09/420,334 entitled "Graphic Design of Combinatorial Material Libraries" (Lacy, et al.) filed on Oct. 18, 1999.

U.S. Patent Application Ser. No. 09/305,830 titled "Synthesizing Combinatorial Libraries of Materials" (Rust, et al.) filed on May 5, 1999.

U.S. Application Ser. No. 09/550,549 entitled "Automated Process Control And Data Management System And Methods" (Crevier, et al.) filed on Apr. 14, 2000.

U.S. Application Ser. No. 09/755,623 entitled "Laboratory Database System and Methods For Combinatorial Materials Research" (Dorsett, Jr., et al.) filed on Jan. 5, 2001.

The family of applications for U.S. Application Ser. No. 09/227,558 entitled, "Apparatus and Method of Research for Creating and Testing Novel Catalysts, Reactions and Polymers" (Turner et al.) filed Jan. 8, 1999.

U.S. Application Ser. No. 09/235,368 entitled "Polymerization Method From the Combinatorial Synthesis and Analysis of Organometallic Compounds and Catalysts" (Weinberg et al.) filed on Jan. 21, 1999.

U.S. Provisional Application Ser. No. 60/122,704 entitled "Controlled, Stable Free Radical Emulsion and Water–Based Polymerizations" (Klaerner et al.) filed on Mar. 9, 1999.

The family of applications for U.S. Application Ser. No. 09/567,598 entitled "Polymer Libraries on a Substrate, Method for Forming Polymer Libraries on a Substrate and Characterization Methods with Same" (Boussie et al.) filed May 10, 2000.

The family of applications for U.S. Patent Application Ser. No. 09/174,856 titled "Graphic Design of Combinatorial Material Libraries" (Lacy, et al.) filed on Oct. 19, 1998.

Odian, Principles of Polymerization, 3rd Ed., John Wiley & Sons, Inc. (1991).

Timoshenko, S., Theory of Plates and Shells, McGraw–Hill, New York 1940.

"DMA 2980 Dynamic Mechanical Analyer," http://www.tainst.com/dma2.html, Dec. 29, 2000.

"Introducing the New DMTA V!", http://www.rheometric-scientific.com/dmtaV.htm, Dec. 29, 2000.

"Standard Test Method for Rubber Property–Intrenational Hardness," American Society for Testing and Materials.

Amitay–Sadovsky, Ella and H. Daniel Wagner, "Evaluation of Young's Modulus of Polymers from Knoop Microindentation Tests" Polymer Communications, 1998, vol. 39, No. 11, pp. 2387–2390.

Calleja, F.J. Balta, "Microhardness Studies of Polymers and Their Transitions" Trip, Dec. 1994, vol. 2, No. 12, pp. 419–425.

Bowl, C., "A Simple Capillary Viscometer" Physics Education, Mar. 1975, vol. 10, No. 2, pp. 102–103.

Lacombe, Robert H. and Jeremy Greenblatt, "Mechanical Propoerties of Thin Polyimide Films" pp. 647–668.

Shinozaki, D.M. and Y. Lu, "Micro–Indentation Relaxation Measurements in Polymer Thin Films" Journal of Electronic Materials, 1997, vol. 26, No. 7, pp. 852–858.

Wierenga, P.E. and A.J.J. Franken, "Ultramicroindentation Apparatus for the Mechanical Characterization of Thin Films" J. Appl. Phys., Jun. 15, 1984, 55 (12).

European Search Report dated Dec. 10, 2001.

U.S. Patent Application Ser. No. 09/939,252 entitled "High Throughput Mechanical Rapid Serial Property Testing of Material Libraries," (P. Mansky) filed on Aug. 24, 2001.

U.S. Patent Application Ser. No. 09/939,139 entitled "High Throughput Fabric Handle Screening," (M. Kossuth et al.) filed on Aug. 24, 2001.

U.S. Patent Application Ser. No. 09/939,149 entitled "High Throughput Rheological Testing of Materials," (P. Mansky et al.) filed on Aug. 24, 2001.

U.S. Patent Application Ser. No. 09/939,263 entitled "High Throughput Mechanical Property Testing of Materials Libraries Using Capacitance," (D. Hajduk et al.) filed on Aug. 24, 2001.

U.S. Patent Application Ser. No. 09/938,994 entitled "High Throughput Mechanical Property Testing of Materials Libraries Using a Piezoelectric," (D. Hajduk) filed on Aug. 24, 2001.

The family of applications for U.S. Patent Application Ser. No. 09/580,024 entitled "Instrument for High Throughput Measurement of Material Physical Properties and Method of Using Same," (Carlson, et al.) filed on May 26, 2000.

*The family of applications for U.S. Patent Application Ser. No. 09/174,856 titled "Graphic Design of Combinatorial Material Libraries"(Lacy, et al.) filed on Oct. 19, 1998.

U.S. Application Ser. No. 09/801,165 entitled "Method and Apparatus for Characterizing Materials By Using a Mechanical Resonator" filed Mar. 7, 2001.

U.S. Application Ser. No. 09/578,997 entitled "High Throughput Viscometer and Method of Using Same" filed May 25, 2000.

*PCT Application No. PCT/US01/11417 entitled "Automated Process Control and Data Management System and Methods", filed Apr. 6, 2001.

*U.S. Application Ser. No. 09/420,334 entitled "Graphic Design of Combinatorial Material Libraries" (Lacy, et al.) filed on Oct. 18, 1999.

*U.S. Patent Application Ser. No. 09/305,830 titled "Synthesizing Combinatorial Libraries of Materials" (Rust, et al.) filed on May 5, 1999.

*U.S. Application Ser. No. 09/550,549 entitled "Automated Process Control And Data Management System And Methods" (Crevier, et al.) filed on Apr. 14, 2000.

*U.S. Application Ser. No. 09/755,623 entitled "Laboratory Database System and Methods For Combinatorial Materials Research" (Dorsett, Jr., et al.) filed on Jan. 5, 2001.

*The family of applications for U.S. Application Ser. No. 09/227,558 entitled, "Apparatus and Method of Research for Creating and Testing Novel Catalysts, Reactions and Polymers" (Turner et al.) filed Jan. 8, 1999.

*The family of applications for U.S. Application Ser. No. 09/211,982 entitled "Parallel Reactor with Internal Sensing" (Turner et al.) filed Dec. 14, 1998.

*U.S. Application Ser. No. 09/235,368 entitled "Polymerization Method From the Combinatorial Synthesis and Analysis of Organometallic Compounds and Catalysts" (Weinberg et al.) filed on Jan. 21, 1999.

*U.S. Provisional Application Ser. No. 60/122,704 entitled "Controlled, Stable Free Radical Emulsion and Water–Based Polymerizations" (Klaerner et al.) filed on Mar. 9, 1999.

The family of applications for U.S. Applicaiton Ser. No. 09/156,827 entitled "Formation of Combinatorial Arrays of Materials Using Solution–Based Methodologies" (Giaquinta et al.) filed Sep. 18, 1998.

*The family of applications of U.S. Application Ser. No. 09/567,598 entitled "Polymer Libraries on a Substrate, Method for Forming Polymer Libraries on a Substrate and Characterization Methods with Same" (Boussie et al.) filed May 10, 2000.

U.S. Application Ser. No. 09/579,338 entitled "Rheo–Optical Indexer and Method of Screening and Characterizing Arrays of Materials" (Carlson et al.) filed on May 25, 2000.

*Odian, Principles of Polymerization, 3rd Ed., John Wiley & Sons, Inc. (1991).

Young, W.C., Roark's Formulas for Stress and Stain, 1989.

*Timoshenko, S., Theory of Plates and Shells, McGraw–Hill, New York 1940.

Osterberg, Peter M. and Stephen D. Senturia, "M–Test: A Test Chip for MEMS Material Property Measurement Using Electrostatically Actuated Test Structures," Journal of Microelectromechanical Systmes, vol. 6, No. 2, Jun. 1997.

Kim, J.O. and B. Lewis Slaten, "Objective Assessment of Fabric Handle in Fabrics Treated With Flame Retardants," Journal of Testing and Evaluation, JTEVA, vol. 24, No. 4, Jul. 1996, pp. 223–228.

Grover, G. et al., "A Screening Technique for Fabric Handle", J. Text. Inst., 1993, 84 No. J. Textile Institute, pp. 486–494.

Pan, Ning and K.C. Yen, "Physical Interpretations of Curves Obtained Through the Fabric Extraction Process for Handle Measurement," Textile Research Journal 62(5), pp. 279–290 (1992).

"Handle–O–Meter", Thwing–Albert Instrument Company, Philadelphia, PA.

Raeel, Mastura and Jiang Liu, "An Empirical Model for Fabric Hand" Textile Research Journal 62, 1, pp. 31–38 (1991).

Ali, S.I. and Shahida Begum, "Fabric Softeners and Softness Perception", Ergonomics, v.37, No. 5, pp. 801–806 (1994).

* cited by examiner

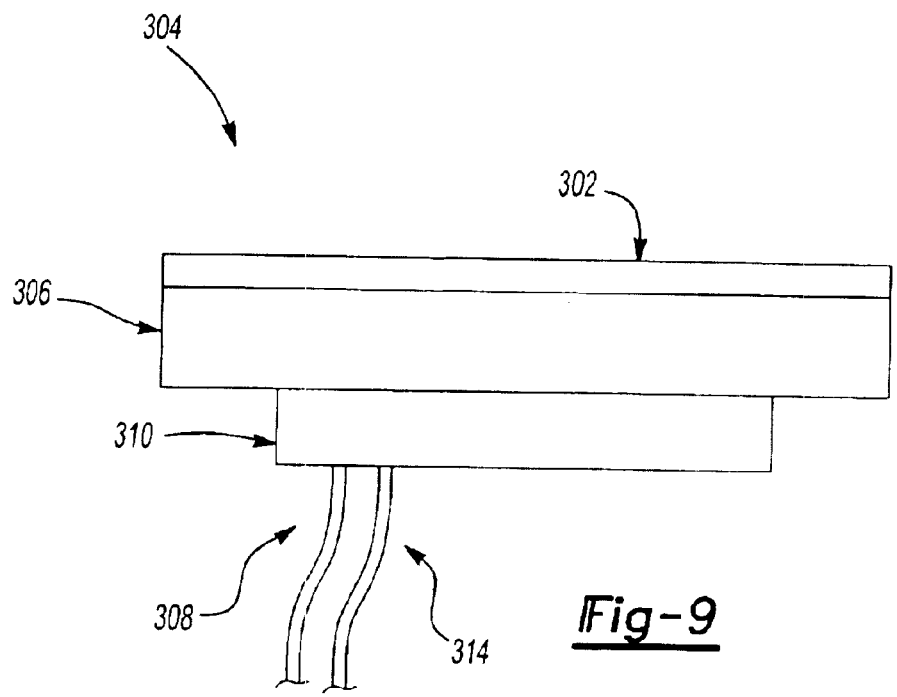
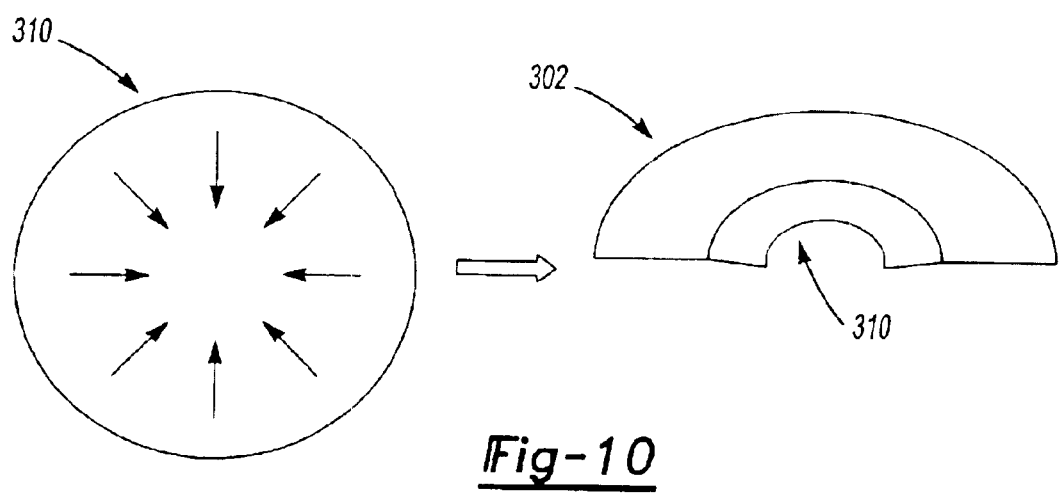

HIGH THROUGHPUT MECHANICAL PROPERTY AND BULGE TESTING OF MATERIALS LIBRARIES

TECHNICAL FIELD

The present invention generally relates to the field of materials characterization. In particular, the invention relates to high throughput screens for evaluating mechanical or physical properties of libraries of polymers or other materials.

BACKGROUND OF THE INVENTION

Currently, there is substantial research activity directed toward the discovery and optimization of polymeric materials for a wide range of applications. Although the chemistry of many polymers and polymerization reactions has been extensively studied, nonetheless, it is rarely possible to predict a priori the physical or chemical properties a particular polymeric material will possess or the precise composition and architecture that will result from any particular synthesis scheme. Thus, characterization techniques to determine such properties are an essential part of the discovery process.

Combinatorial chemistry refers generally to methods for synthesizing a collection of chemically diverse materials and to methods for rapidly testing or screening this collection of materials for desirable performance characteristics and properties. Combinatorial chemistry approaches have greatly improved the efficiency of discovery of useful materials. For example, material scientists have developed and applied combinatorial chemistry approaches to discover a variety of novel materials, including for example, high temperature superconductors, magnetoresistors, phosphors and catalysts. See, for example, U.S. Pat. No. 5,776,359 (Schultz, et al). In comparison to traditional materials science research, combinatorial materials research can effectively evaluate much larger numbers of diverse compounds in a much shorter period of time. Although such high-throughput synthesis and screening methodologies are conceptually promising, substantial technical challenges exist for application thereof to specific research and commercial goals.

The characterization of polymers or other materials using combinatorial methods has only recently become known. Examples of such technology are disclosed, for example, in commonly owned U.S. Pat. Nos. 6,182,499 (McFarland, et al); 6,175,409 B1 (Nielsen, et al); 6,157,449 (Hajduk); 6,151,123 (Nielsen); 6,034,775 (McFarland, et al); 5,959,297 (Weinberg, et al), all of which are hereby expressly incorporated by reference herein.

Of particular interest to the present invention are combinatorial methods and apparatuses for screening polymers and other materials for physical or mechanical characteristics. Screening of the materials for mechanical properties presents a multitude of challenges. As an example, conventional instruments, such as conventional stress or strain testing machines and other apparatuses traditionally lack the ability to screen mechanical properties of several materials in rapid succession, in parallel, on a single substrate or a combination thereof. Thus, challenges are presented for forming systems that can quickly process and test (either in parallel or in serial succession) mechanical properties of many materials.

SUMMARY OF THE INVENTION

The present invention provides instruments and methods for screening combinatorial libraries that addresses many of the problems encountered when using conventional instruments. For example, the disclosed instruments can measure mechanical properties of library members in rapid serial or parallel test format, and can perform tests on small amounts of material, which are easily prepared or dispensed using art-disclosed liquid or solid handling techniques. Compared to conventional instruments, the disclosed instruments afford faster sample loading and unloading, for example, through the use of disposable libraries of material samples.

Thus, one aspect of the present invention provides instruments for measuring mechanical properties of a combinatorial library of materials. The instruments include at least one mounting member to which the library of material samples is removably secured for testing; at least one source selected from the group consisting of a fluid, a voltage, a piezoelectric and a combination thereof for delivering one or more forces to each library member; and at least one sensing device for monitoring the response each library member to the one or more forces.

Another aspect of the present invention provides methods of screening a combinatorial library of materials. In a preferred embodiment, the methods include providing a combinatorial library of materials comprising at least four different samples, and delivering one or more forces to at least two of the samples simultaneously by a source selected from the group consisting of a fluid, a voltage, a piezoelectric and a combination thereof. The methods further include monitoring the response of each library member to the one or more forces. In another preferred embodiment, the method includes providing a combinatorial library of materials having at least four different samples; delivering one or more force to each of the samples serially by a source selected from the group consisting of a fluid, a voltage, a piezoelectric and a combination thereof; and monitoring the response of each library member to the one or more forces at a throughput rate no greater than about 10 minutes per sample. Depending on the type of force applied, the methods can screen libraries of materials for a variety of mechanical properties related to Young's modulus (e.g., flexure, uniaxial extension, biaxial compression, and shear), failure (stress and strain at failure, toughness), adhesion, or others.

BRIEF DESCRIPTION OF THE DRAWINGS

FIG. 9 shows a side view of one embodiment of a piezoelectric bender that can be used in the piezoelectric instrument shown in FIG. 7.

FIG. 10 shows the response of the piezoelectric bender shown in FIG. 9 when voltage is applied to it.

DETAILED DESCRIPTION OF THE PREFERRED EMBODIMENTS

Glossary

Figure 1:
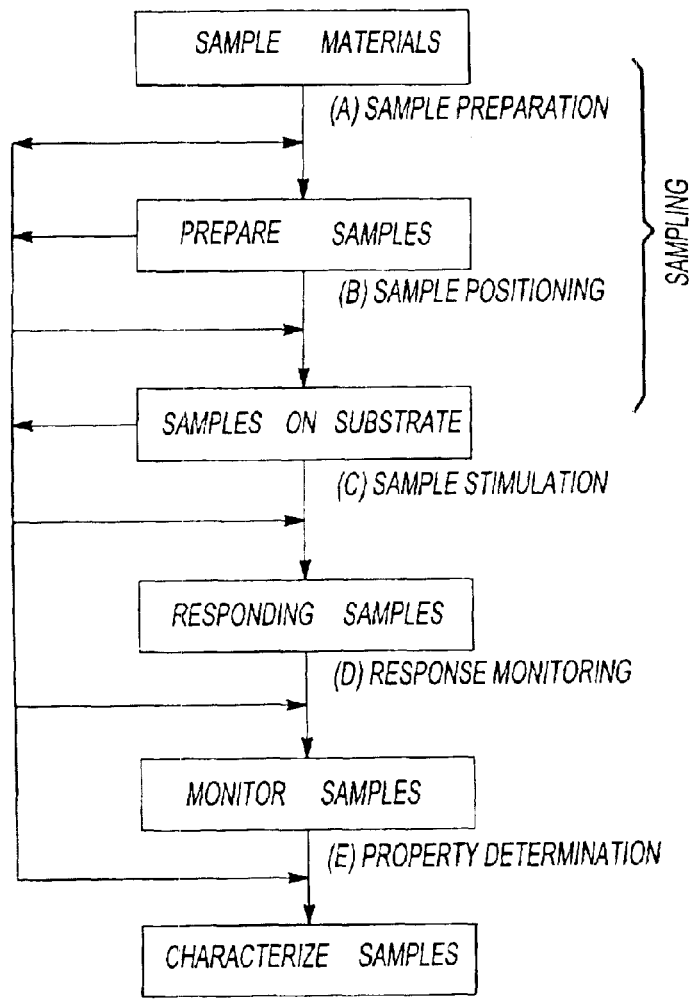
FIG. 1 shows a flowchart of possible steps for methods of the present invention.

The following terms are intended to have the following general meanings as they are used herein.

1. Fluid: The term "fluid" refers to a gas or a liquid.
2. Mixture: The term "mixture" refers to a collection of molecules, ions, electrons, chemical substances, etc. Each component in the mixture can be independently varied. A mixture can consist of two or more substances intermingled with no constant percentage composition, wherein each component may or may not retain its essential original properties, and where molecular phase mixing may or may not occur. In mixtures, the components making up the mixture may or may not remain distinguishable from each other by virtue of their chemical structure.

These and other aspects of the invention are to be considered exemplary and non-limiting, and are discussed in greater detail below. The several aspects of the characterization instruments and methods disclosed and claimed herein can be advantageously employed separately, or in combination to efficiently characterize a variety of materials, with particular emphasis on solid materials and polymeric materials. In preferred embodiments, these features are employed in combination to form a materials characterization system that can operate as a high-throughput screen in a combinatorial materials science research program directed to identifying and optimizing new materials. Such materials appropriate for combinatorial research may include, for instance, polymers, catalysts, products of various polymerization reaction conditions, lubricants, gels, adhesives, coatings and/or products of new post-synthesis processing conditions. Other materials appropriate for combinatorial research according to the present invention may include, but are not limited to, foodstuffs, cosmetics, beverages, lotions, creams, pharmaceuticals, inks, body fluids, fuels, additives, detergents, surfactants, shampoos, conditioners, dyes, waxes, electrolytes, fuel cell electrolytes, photoresist, semiconductor material, wire coatings, hair styling products and the like.

Combinatorial Approaches for Science Research

In a combinatorial approach for identifying or optimizing materials or reactions, a large compositional space (e.g., in the context of polymers; of monomers, comonomers, catalysts, catalyst precursors, solvents, initiators, additives, or of relative ratios of two or more of the aforementioned) or a large reaction condition space (e.g., of temperature, pressure and reaction time) may be rapidly explored by preparing libraries and then rapidly screening such libraries. By way of illustration, polymer libraries can comprise, for example, polymerization product mixtures resulting from polymerization reactions that are varied with respect to such factors.

For example, in the context of polymers (but also applicable to other materials), combinatorial approaches for screening a polymer library can include an initial, primary screening, in which polymerization products are rapidly evaluated to provide valuable preliminary data and, optimally, to identify several "hits"—particular candidate materials having characteristics that meet or exceed certain predetermined metrics (e.g., performance characteristics, desirable properties, unexpected and/or unusual properties, etc.). Such metrics may be defined, for example, by the characteristics of a known or standard polymer or polymerization scheme. Because local performance maxima may exist in compositional spaces between those evaluated in the primary screening of the first libraries or alternatively, in process-condition spaces different from those considered in the first screening, it may be advantageous to screen more focused polymer libraries (e.g., libraries focused on a smaller range of compositional gradients, or libraries comprising compounds having incrementally smaller structural variations relative to those of the identified hits) and additionally or alternatively, subject the initial hits to variations in process conditions. Hence, a primary screen can be used reiteratively to explore localized and/or optimized compositional space in greater detail. The preparation and evaluation of more focused polymer libraries can continue as long as the high-throughput primary screen can meaningfully distinguish between neighboring library compositions or compounds.

Once one or more hits have been satisfactorily identified based on the primary screening, polymer and polymerization product libraries focused around the primary-screen hits can be evaluated with a secondary screen—a screen designed to provide (and typically verified, based on known materials, to provide) chemical composition or process conditions that relate with a greater degree of confidence to commercially-important processes and conditions than those applied in the primary screen. In many situations, such improved "real-world-modeling" considerations are incorporated into the secondary screen at the expense of methodology speed (e.g., as measured by sample throughput) compared to a corresponding primary screen. Particular polymer materials, catalysts, reactants, polymerization conditions or post-synthesis processing conditions having characteristics that surpass the predetermined metrics for the secondary screen may then be considered to be "leads." If desired, additional polymer or polymerization product libraries focused about such lead materials can be screened with additional secondary screens or with tertiary screens. Identified lead polymers, monomers, catalysts, catalyst precursors, initiators, additives or reaction conditions may be subsequently developed for commercial applications through traditional bench-scale and/or pilot scale experiments.

While the concept of primary screens and secondary screens as outlined above provides a valuable combinatorial research model for investigating polymers and polymerization reactions, a secondary screen may not be necessary for certain chemical processes where primary screens provide an adequate level of confidence as to scalability and/or where market conditions warrant a direct development approach. Similarly, where optimization of materials having known properties of interest is desired, it may be appropriate to start with a secondary screen. In general, the systems, devices and methods of the present invention may be applied as either a primary, secondary or other screen, depending on the specific research program and goals thereof. See, generally, U.S. patent application Ser. No. 09/227,558 entitled "Apparatus and Method of Research for Creating and Testing Novel Catalysts, Reactions and Polymers", filed Jan. 8, 1999 by Turner, et al., for further discussion of a combinatorial approach to polymer science research. Bulk quantities of a particular material may be made after a primary screen, a secondary screen, or both.

According to the present invention, methods, systems and devices are disclosed that improve the efficiency and/or effectiveness of the steps necessary to characterize mechanical or physical properties of a material sample or a plurality of samples. In preferred embodiments, in the context of polymer analysis, a property of a plurality of polymer samples or of components thereof can be detected in a polymer characterization system with an average sample—throughput sufficient for an effective combinatorial polymer science research program.

Referring to FIG. 1, the systems and methods, preferably, start with a library or array of sample materials that may exhibit one or more predetermined physical/mechanical properties. Ultimately, these predetermined properties will be determined in a determination step (Step E), however, several prior steps may be effected prior to Step E. The sample materials may be prepared such as by heating, cooling, or addition of additives. Such preparation is typically designed to affect the properties that are ultimately being determined. The sample materials may also be positioned in a desirable manner for property determination. The materials may be positioned on a substrate, a machine or otherwise positioned to assist in ultimately determining properties of the materials.

It will be appreciated that one of the advantageous features of the present invention is that it affords the ability to screen newly created materials some or all of which are uncharacterized or whose properties are unknown prior to the time of screening. Thus, previously unidentified and uncharacterized new materials can be screened for a common selected property. However, this does not prevent the employment of known references controls or standard as among the library members.

It shall be recognized that sample preparation (Step A) and sample positioning (Step B) may be optional steps in property determination protocols. Also sample preparation and sample positioning may be performed in any order if they are performed. Additionally it should be recognized that sequences other than the order of steps listed above are possible, and the above listing is not intended as limiting.

Typically, however, stimulation of the sample materials (Step C) is needed to effect one or more responses of the materials wherein the responses are related to the one or more physical properties that are being tested. Exemplary stimuli include force, contact, motion and the like. Exemplary responses include flow, or resistance to flow, deflection, adhesion, deformation, rupture or the like. Negative forces (e.g., compression as opposed to tension, negative pressure as opposed to positive pressure) or the like may be employed.

The responses of the materials are typically monitored (Step D) with hardware such as sensors, transducers, load cells or other like devices. Properties may be determined (Step E) quantitatively or qualitatively by relating the responses to the material properties.

A plurality of samples may be characterized as described above in connection with FIG. 1. As a general approach for improving the sample throughput for a plurality of samples, each of the steps (A) through (E) of FIG. 1 applicable to a given characterization protocol can be optimized with respect to time and quality of information, both individually and in combination with each other. Additionally or alternatively, each or some of such steps can be effected in a rapid-serial, parallel, serial-parallel or hybrid parallel-serial manner.

The throughput of a plurality of samples through a single step in a characterization process is improved by optimizing the speed of that step, while maintaining—to the extent necessary—the information-quality aspects of that step.

Although conventional research norms, developed in the context in which research was rate-limited primarily by the synthesis of samples, may find such an approach less than wholly satisfactory, the degree of rigor can be entirely satisfactory for a primary or a secondary screen of a combinatorial library of samples. For combinatorial research (and as well, for many on-line process control systems), the quality of information should be sufficiently rigorous to provide for scientifically acceptable distinctions between the compounds or process conditions being investigated, and for a secondary screen, to provide for scientifically acceptable correlation (e.g., values or, for some cases, trends) with more rigorous, albeit more laborious and time-consuming traditional characterization approaches.

The throughput of a plurality of samples through a series of steps, where such steps are repeated for the plurality of samples, can also be optimized. In one approach, one or more steps of the cycle can be compressed relative to traditional approaches or can have leading or lagging aspects truncated to allow other steps of the same cycle to occur sooner compared to the cycle with traditional approaches. In another approach, the earlier steps of a second cycle can be performed concurrently with the later steps of a first cycle. For example, in a rapid-serial approach for characterizing a sample, sample preparation, delivery to a substrate or the like, for a second sample in a series can be effected before or while the first sample in the series is being screened. As another example, a screen of a second sample in a series can be initiated while the first sample in the series is being screened.

A characterization protocol for a plurality of samples can involve a single-step process (e.g., direct measurement of a property of a sample or of a component thereof) or several steps. In a rapid-serial screen approach for a single-step process, the plurality of samples and a single measuring instrument or other instruments are serially positioned in relation to each other for serial analysis of the samples. In a parallel analysis approach, (e.g., as might be employed by itself, or in an upstream or downstream analysis of the samples relative to a rapid-serial analysis of the present invention) two or more measuring instruments or other apparatus are employed to measure properties of two or more samples simultaneously.

In a serial-parallel approach, a property of a larger number of samples (e.g., four or more) is screened as follows. First, a property of a subset of the four or more samples (e.g., 2 samples) is screened in parallel for the subset of samples, and then serially thereafter, a property of another subset of four or more samples is screened in parallel. It will be recognized, of course, that plural measuring instruments can be employed simultaneous, or plural measuring instruments can be employed serially.

For characterization protocols involving more than one step, optimization approaches to effect high-throughput characterization can vary. As one example, a plurality of samples can be characterized with a single characterization system (I) in a rapid-serial approach in which each of the plurality of samples ($s_1, s_2, s_3 \ldots s_n$) are processed serially through the characterization system (I) with each of the steps effected in series on each of the of samples to produce a serial stream of corresponding characterizing property information ($p_1, p_2, p_3 \ldots p_n$). This approach benefits from minimal capital investment, and may provide sufficient throughput—particularly when the steps have been optimized with respect to speed and quality of information.

As another example, a plurality of samples can be characterized with two or more instruments in a pure parallel (or for larger libraries, serial-parallel) approach in which the plurality of samples ($s_1, s_2, s_3 \ldots s_n$) or a subset thereof are processed through the two or more measurement systems (I, II, III . . . N) in parallel, with each individual system effecting each step on one of the samples to produce the property information ($p_1, p_2, p_3 \ldots p_n$) in parallel. This approach is advantageous with respect to overall throughput, but may be constrained by the required capital investment.

In a hybrid approach, certain of the steps of the characterization process can be effected in parallel, while certain other steps can be effected in series. Preferably, for example, it may be desirable to effect the longer, throughput-limiting steps in parallel for the plurality of samples, while effecting the faster, less limiting steps in series. Such a parallel-series hybrid approach can be exemplified by parallel sample preparation of a plurality of samples ($s_1, s_2, s_3 \ldots s_n$), followed by measuring with a single apparatus to produce a serial stream of corresponding characterizing property information ($p_1, p_2, p_3 \ldots p_n$). In another exemplary parallel-series hybrid approach, a plurality of samples ($s_1, s_2, s_3 \ldots s_n$) are prepared, measured and correlated in a slightly offset (staggered) parallel manner to produce the characterizing property information ($p_1, p_2, p_3 \ldots p_n$) in the same staggered-parallel manner.

Optimization of individual characterization steps with respect to speed and quality of information can improve sample throughput regardless of whether the overall characterization scheme involves a rapid-serial or parallel aspect (i.e., true parallel, serial-parallel or hybrid parallel-series approaches). As such, the optimization techniques disclosed hereinafter, while discussed primarily in the context of a rapid-serial approach, are not limited to such an approach, and will have application to schemes involving parallel characterization protocols that may be employed.

Sample Materials

The samples for which the present invention is useful for screening include polymeric materials or any other liquid, semi-solid, or solid material that is capable of being provided as a high viscosity fluid, solid, or other suitable form. Accordingly, without limitation, pure materials, mixtures of materials, bulk materials, particles of materials, thin films of materials, dispersions of materials, emulsions of materials, and solutions of materials are all contemplated as within the useful scope of the present invention.

In a particularly preferred embodiment, the present invention is employed for screening polymer samples, or plastic samples including polymers. Accordingly, unless otherwise stated, reference to screening of polymers or other processing of polymers includes plastics incorporating such polymers. The polymer sample can be a homogeneous polymer sample or a heterogeneous polymer sample, and in either case, comprises one or more polymer components. As used herein, the term "polymer component" refers to a sample component that includes one or more polymer molecules. The polymer molecules in a particular polymer component can have the same repeat unit, and can be structurally identical to each other or structurally different from each other. For example, a polymer component may comprise a number of different molecules, with each molecule having the same repeat unit, but with a number of molecules having different molecular weights from each other (e.g., due to a different degree of polymerization). As another example, a heterogeneous mixture of copolymer molecules may, in some cases, be included within a single polymer component (e.g., a copolymer with a regularly-occurring repeat unit), or may, in other cases, define two or more different polymer components (e.g., a copolymer with irregularly-occurring or randomly-occurring repeat units). Hence, different polymer components include polymer molecules having different repeat units. It is possible that a particular polymer sample (e.g., a member of a library) will not contain a particular polymer molecule or polymer component of interest.

In one embodiment, the polymer molecule of the polymer component is preferably, but need not be, a non-biological polymer. A non-biological polymer is, for purposes herein, a polymer other than an amino-acid polymer (e.g., protein) or a nucleic acid polymer (e.g., deoxyribonucleic acid (DNA)). However, the employment of the present invention for screening of materials for use as biological implants or prosthetics is contemplated. For instance, the ability of a biological polymer to bind to an agent may be determined from the mechanical property response of a sample of the material in the presence of such agent. The polymer molecule of the polymer component is, however, not generally critical; that is, the systems and methods disclosed herein will have broad application with respect to the type (e.g., architecture, composition, synthesis method or mechanism) and/or nature (e.g., physical state, form, attributes) of the polymer. Hence, the polymer molecule can be, with respect to homopolymer or copolymer architecture, a linear polymer, a branched polymer (e.g., short-chain branched, long-chained branched, hyper-branched), a cross-linked polymer, a cyclic polymer or a dendritic polymer. A copolymer molecule can be a random copolymer molecule, a block copolymer molecule (e.g., di-block, tri-block, multi-block, taper-block), a graft copolymer molecule or a comb copolymer molecule.

The particular composition of the polymer molecule is not critical. The material may be thermoplastic, thermoset or a mixture thereof. It may be a polycondensate, polyadduct, a modified natural polymer. Exemplary materials include polymers incorporating olefins, styrenes, acrylates, methacrylates, polyimides, polyamides, epoxies, silicones, phenolics, rubbers, halogenated polymers, polycarbonates, polyketones, urethanes, polyesters, silanes, sulfones, allyls, polyphenylene oxides, terphthalates, or mixtures thereof. Other specific illustrative examples can include repeat units or random occurrences of one or more of the following, without limitation: polyethylene, polypropylene, polystyrene, polyolefin, polyamide, polyimide, polyisobutylene, polyacrylonitrile, poly(vinyl chloride), poly(methyl methacrylate), poly(vinyl acetate), poly (vinylidene chloride), polytetrafluoroethylene, polyisoprene, polyacrylamide, polyacrylic acid, polyacrylate, poly(ethylene oxide), poly(ethyleneimine), polyamide, polyester, polyurethane, polysiloxane, polyether, polyphosphazine, polymethacrylate, and polyacetals. Polysaccharides are also preferably included within the scope of polymers. Exemplary naturally-occurring polysaccharides include cellulose, dextran, gums (e.g., guar gum, locust bean gum, tamarind xyloglucan, pullulan), and other naturally-occurring biomass. Exemplary semi-synthetic polysaccharides having industrial applications include cellulose diacetate, cellulose triacetate, acylated cellulose, carboxymethyl cellulose and hydroxypropyl cellulose. In any case, such naturally-occurring and semi-synthetic polysaccharides can be modified by reactions such as hydrolysis, esterification, alkylation, or by other reactions.

In typical applications, a polymer sample is a heterogeneous sample comprising one or more polymer components, one or more monomer components and/or and an additional phase which may be a continuous fluid phase. In copolymer applications, the polymer sample can comprise one or more copolymers, a first comonomer, a second comonomer, additional comonomers, and/or a continuous fluid phase. The polymer samples can, in any case, also include other components, such as catalysts, catalyst precursors (e.g., ligands, metal-precursors), solvents, initiators, additives, products of undesired side-reactions (e.g., polymer gel, or undesired homopolymer or copolymers) and/or impurities. Typical additives include, for example, surfactants, fillers, reinforcements, flame retardants, colorants, environmental protectants, other performance modifiers, control agents, plasticizers, cosolvents and/or accelerators, among others. In this regard, the present invention is particularly attractive for the screening of effects of variations of additives upon the characteristics of the material. The various components of the heterogeneous polymer sample can be uniformly or non-uniformly dispersed in the continuous fluid phase.

In one preferred embodiment, the polymer samples of the present invention are melted or otherwise heated to a high viscosity fluid state, with the resulting material constituting a high viscosity fluid sample. Heating may be performed simultaneously while the samples are on a common substrate. Alternatively, the sample is heated to liquefy it or maintain its liquidity while being transferred to a common substrate (e.g., while in a probe of an automated sampler).

In another embodiment at a point prior to, during, or after depositing the sample onto the substrate, the polymer sample is preferably, chemically treated to form a liquid polymer sample, such as a polymer solution, a polymer emulsion, a polymer dispersion or a polymer that is liquid in the pure state (i.e., a neat polymer). A polymer solution comprises one or more polymer components dissolved in a solvent. The polymer solution can be of a form that includes well-dissolved chains and/or dissolved aggregated micelles. The solvent can vary, depending on the application, for example with respect to polarity, volatility, stability, and/or inertness or reactivity. Typical solvents include, for example, tetrahydrofuran (THF), toluene, hexane, ethers, trichlorobenzene, dichlorobenzene, dimethylformamide, water, aqueous buffers, alcohols, etc. According to traditional chemistry conventions, a polymer emulsion can be considered to comprise one or more liquid-phase polymer components emulsified (uniformly or non-uniformly) in a liquid continuous phase, and a polymer dispersion can be considered to comprise solid particles of one or more polymer components dispersed (uniformly or non-uniformly) in a liquid continuous phase. The polymer emulsion and the polymer dispersion can also be considered, however, to have the more typically employed meanings specific to the art of polymer science—of being an emulsion-polymerization product and dispersion-polymerization product, respectively. In such cases, for example, the emulsion polymer sample can more generally include one or more polymer components that are insoluble, but uniformly dispersed, in a continuous phase, with typical emulsions including polymer component particles ranging in diameter from about 1 nm to about 500 nm, more typically from about 5 nm to about 300 nm, and even more typically from about 40 nm to about 200 nm. The dispersion polymer sample can, in such cases, generally include polymer component particles that are dispersed (uniformly or nonuniformly) in a continuous phase, with typical particles having a diameter ranging from about 0.2 um to about 1000 um, more typically from about 0.4 um to about 500 um, and even more typically from about 0.5 um to about 200 um. Exemplary polymers that can be in the form of neat polymer samples include dendrimers, and siloxane, among others. The high viscosity fluid polymer sample can also be employed in the form of a slurry, a latex, a microgel, a physical gel, or in any other form sufficient for creating an array for screening analysis as described and claimed herein. In some cases, polymer synthesis reactions (i.e., polymerizations) directly produce high viscosity fluid samples. In other cases, the polymer may be synthesized, stored or otherwise available for characterization in a non-liquid physical state, such as a solid state (e.g., crystalline, semicrystalline or amorphous), a glassy state or rubbery state. The polymer sample can, regardless of its particular form, have various attributes, including variations with respect to polarity, solubility and/or miscibility.

In preferred applications, the polymer sample is a polymerization product mixture. As used herein, the term "polymerization product mixture" refers to a mixture of sample components obtained as a product from a polymerization reaction. An exemplary polymerization product mixture can be a sample from a combinatorial library prepared by polymerization reactions, or can be a polymer sample drawn off of an industrial process line. In general, the polymer sample may be obtained after the synthesis reaction is stopped or completed or during the course of the polymerization reaction. Alternatively, samples of each polymerization reaction can be taken and placed into an intermediate vessels at various times during the course of the synthesis, optionally with addition of more solvent or other reagents to arrest the synthesis reaction or prepare the samples for analysis. These intermediate samples can then be characterized at any time without interrupting the synthesis reaction.

It is also possible to use polymer samples or libraries of polymer samples that were prepared previously and stored. Typically, polymer libraries can be stored with agents to ensure polymer integrity. Such storage agents include, for example, antioxidants or other agents effective for preventing cross-linking of polymer molecules during storage. Depending upon the polymerization reaction, other processing steps may also be desired, all of which are preferably automated.

The polymerization scheme and/or mechanism by which the polymer molecules of the polymer component of the sample are prepared is not critical, and can include, for example, reactions considered to be addition polymerization, condensation polymerization, step-growth polymerization, and/or chain-growth polymerization reactions. Viewed from another aspect, the polymerization reaction can be an emulsion polymerization or a dispersion polymerization reaction. Viewed more specifically with respect to the mechanism, the polymerization reaction can be free radical polymerization, ionic polymerization (e.g., cationic polymerization, anionic polymerization), and/or ring-opening polymerization reactions, among others. Non-limiting examples of the foregoing include, Ziegler-Natta or Kaminsky-Sinn reactions and various copolymerization reactions. Polymerization product mixtures can also be prepared by modification of a polymeric starting materials, by grafting reactions, chain extension, chain scission, functional group interconversion, or other reactions.

It will be appreciated that in certain embodiments, a polymer sample is formed in situ on a substrate, post synthesis treated in situ on a substrate, or a combination thereof. Examples of such post synthesis treatment steps include for instance, heat treating, environmental exposure (e.g., temperature moisture, radiation, chemicals, etc.), aged, or the like.

In other preferred embodiments, polymer or other sample materials may be provided as solids or semi-solids. Such samples may be provided in a variety of geometric configurations such as blocks, cylinders, loops, films and the like.

Generally, geometric configurations are selected to be appropriate for one or more tests that are to be performed upon the samples. Solid and semi-solid samples may be rigid, elastic, gelatinous or otherwise. In one preferred embodiment, samples are provided in a tacky state, and thus exhibits at least some degree of adhesiveness within the range of temperature under examination. Samples may also be specifically arranged for testing. For example, samples may be interwoven as a fabric, unwoven, machined to shape, molded to shape, cut to shape or otherwise physically manipulated for testing.

Sample Size

The sample size is not narrowly critical, and can generally vary, depending on the particular characterization protocols and systems used to analyze the sample or components thereof. However, it will be appreciated that the present invention advantageously permits for attaining reliable data with relatively small samples. Typical sample sizes can range from about 0.1 microgram to about 1 gram, more typically from about 1 microgram to about 100 milligrams, even more typically from about 5 micrograms to about 1000 micrograms, and still more typically from about 20 micrograms to about 50 micrograms.

If and when placed on a substrate for forming a library, as discussed herein with regard to sampling, the samples may be dispensed with any suitable dispensing apparatus (e.g., an automated micropipette or capillary dispenser, optionally with a heated tip). Each sample of the library is dispensed to an individually addressable region on the substrate. Generally, each sample occupies no more than about 1000 mm$^2$ of area on a substrate surface, preferably no more than about 100 mm$^2$, more preferably no more than about 50 mm$^2$, even more preferably no more than about 10 mm$^2$, most preferably no more than about 5 mm$^2$, and it is possible for a sample to occupy less than about 1 mm$^2$. The sample is preferably to have a thickness that is less than about 500 microns, preferably less than about 100 microns, even more preferably less than about 10 microns, most preferably less than about 5 microns, and it is possible for a sample to have a thickness that is less than about 1 microns.

In applications where the sample is disposed in a well, preferably the sample size does not exceed about 1000 milligrams. Accordingly, for dispensing high viscosity fluid samples, the individual samples are each dispensed in amounts no greater than about 100 ml, more preferably no greater than about 10 ml and still more preferably no greater than about 1 ml.

Libraries of Sample Materials

Libraries of samples have 2 or more samples that are physically or temporally separated from each other—for example, by residing in different regions of a common substrate, in different substrates, in different sample containers of a common substrate, by having a membrane or other partitioning material positioned between samples, or otherwise. The plurality of samples preferably has at least 4 samples and more at least 8 samples. Four samples can be employed, for example, in connection with experiments having one control sample and three polymer samples varying (e.g., with respect to composition or process conditions as discussed above) to be representative of a high, a medium and a low-value of the varied factor—and thereby, to provide some indication as to trends. Four samples are also a minimum number of samples to effect a serial-parallel characterization approach, as described above (e.g., with two analytical instruments operating in parallel). Eight samples can provide for additional variations in the explored factor space. Moreover, eight samples corresponds to the number of parallel polymerization reactors in the PPR-8™, being selectively offered as one of the Discovery Tools™ of Symyx Technologies, Inc. (Santa Clara, Calif.), which can be used to prepare polymers for screening in accordance with the present invention. Higher numbers of samples can be investigated, according to the methods of the invention, to provide additional insights into larger compositional and/or process space. In some cases, for example, the plurality of samples can be 15 or more samples, preferably 20 or more samples, more preferably 40 or more samples and even more preferably 80 or more samples. Such numbers can be loosely associated with standard configurations of other parallel reactor configurations for synthesizing materials for screening herein (e.g., the PPR-48™, Symyx Technologies, Inc.) or of standard sample containers (e.g., 96-well microtiter plate-type formats). Moreover, even larger numbers of samples can be characterized according to the methods of the present invention for larger scale research endeavors. Hence, for screening of polymers or other materials the number of samples can be 150 or more, 400 or more, 500 or more, 750 or more, 1,000 or more, 1,500 or more, 2,000 or more, 5,000 or more and 10,000 or more samples. As such, the number of samples can range from about 2 samples to about 10,000 samples or more, and preferably from about 8 samples to about 10,000 or more samples. In many applications, however, the number of samples can range from about 80 samples to about 1500 samples.

In some cases, in which processing of samples using typical 96-well microtiter-plate formatting or scaling is convenient or otherwise desirable, the number of samples can be 96*N, where N is an integer ranging from about 1 to about 100 or greater. For many applications, N can suitably range from 1 to about 20, and in some cases, from 1 to about 5.

A library of samples comprises two or more different samples spatially separated—preferably, but not necessarily on a common substrate, or temporally separated. Candidate samples (i.e., members) within a library may differ in a definable and typically predefined way, including with regard to chemical structure, processing (e.g., synthesis) history, mixtures of interacting components, post-synthesis treatment, purity, etc. The samples are spatially separated, preferably at an exposed surface of the substrate, such that the library of samples is separately addressable for characterization thereof. The two or more different samples can reside in sample containers formed as wells in a surface of the substrate. The number of samples included within the library can generally be the same as the number of samples included within the plurality of samples, as discussed above. In general, however, not all of the samples within a library of samples need to be different samples. When process conditions are to be evaluated, the libraries may contain only one type of sample. The use of reference standards, controls or calibration standards may also be performed, though it is not necessary. Further, a library may be defined to include sub-groups of members of different libraries, or it may include combinations of plural libraries. The samples of a library may be previously characterized, uncharacterized or a combination thereof, so that property information about the samples may not be known before screening.

Typically, for combinatorial science research applications, at least two or more, preferably at least four or more, even more preferably eight or more and, in many cases, most preferably each of the plurality of polymer samples in a given library of samples will be different from each other. Specifically, a different sample can be included within at least about 50%, preferably at least 75%, preferably at least 80%, even more preferably at least 90%, still more preferably at least 95%, yet more preferably at least 98% and most preferably at least 99% of the samples included in the sample library. In some cases, all of the samples in a library of samples will be different from each other.

In one embodiment, preferably at least eight samples are provided in a library on a substrate and at least about 50% of the samples included in the library are different from each other. More preferably, the library includes at least 16 samples and at least 75% of said samples included in said library are different from each other. Still more preferably, the library includes at least 48 samples and at least 90% of said samples included in the library are different from each other.

The substrate can be a structure having a rigid or semi-rigid surface on which or into which the library of samples can be formed, mounted, deposited or otherwise positioned. The substrate can be of any suitable material, and preferably includes materials that are inert with respect to the samples of interest, or otherwise will not materially affect the mechanical or physical characteristics of one sample in an array relative to another. Exemplary polymeric materials that can be suitable as a substrate material in particular applications include polyimides such as Kapton™., polypropylene, polytetrafluoroethylene (PTFE) and/or polyether etherketone (PEEK), among others. The substrate material is also preferably selected for suitability in connection with known fabrication techniques. Metal or ceramic (e.g., stainless steel, silicon, including polycrystalline silicon, single-crystal silicon, sputtered silicon, and silica ($SiO_2$) in any of its forms (quartz, glass, etc.)) are also preferred substrate materials. Other known materials (e.g., silicon nitride, silicon carbide, metal oxides (e.g., alumina), mixed metal oxides, metal halides (e.g., magnesium chloride), minerals, zeolites, and ceramics) may also be suitable for a substrate material in some applications. Another suitable substrate is a silicon wafter that has been patterned to define a predetermined configuration on which the sample or samples are deposited (e.g., suspended deflectable arms). As to form, the sample containers formed in, at or on a substrate can be preferably, but are not necessarily, arranged in a substantially flat, substantially planar surface of the substrate. The sample containers can be formed in a surface of the substrate as dimples, spots, wells, raised regions, trenches, or the like. Non-conventional substrate-based sample containers, such as relatively flat surfaces having surface-modified regions (e.g., selectively wettable regions) can also be employed. The overall size and/or shape of the substrate is not limiting to the invention. The size and shape can be chosen, however, to be compatible with commercial availability, existing fabrication techniques, and/or with known or later-developed automation techniques, including automated sampling and automated substrate-handling devices. The substrate is also preferably sized to be portable by humans. The substrate can be thermally insulated, particularly for high-temperature and/or low-temperature applications.

In certain preferred embodiments, the substrate is formed to securely maintain contact with a plurality of samples. According to various methodologies it may be desirable to place forces on samples while the samples remain secured to the substrate. Forces may be applied to the samples by one or more members separate from the substrate or the substrate may apply the forces.

In one particularly preferred embodiment, the library includes a combinatorial library of polymerization product mixtures. Polymer libraries can comprise, for example, polymerization product mixtures resulting from polymerization reactions that are varied with respect to, for example, reactant materials (e.g., monomers, comonomers), catalysts, catalyst precursors, initiators, additives, the relative amounts of such components, reaction conditions (e.g., temperature, pressure, reaction time), post-synthesis treatment, or any other factor affecting polymerization or material properties. Design variables for polymerization reactions are well known in the art. See generally, Odian, Principles of Polymerization, 3rd Ed., John Wiley & Sons, Inc. (1991). A library of polymer samples may be prepared in parallel polymerization reactors or in a serial fashion. Exemplary methods and apparatus for preparing polymer libraries—based on combinatorial polymer synthesis approaches—are disclosed in copending U.S. patent application Ser. No. 09/211,982 of Turner, et al., filed on Dec. 14, 1998, copending U.S. patent application Ser. No. 09/227,558 of Turner, et al., filed on Jan. 8, 1999, copending U.S. patent application Ser. No. 09/235,368 of Weinberg, et al., filed on Jan. 21, 1999, and copending U.S. Provisional Patent Application Serial No. 60/122,704 entitled "Controlled, Stable Free Radical Emulsion and Water-Based Polymerizations", filed on Mar. 9, 1999 by Klaerner, et al. See also, PCT Patent Application WO 96/11878.

Non-Polymer Sample Materials

Although several of the primary applications of the present invention are directed to combinatorial polymer science research and/or quality control for industrial polymer synthesis or processing protocols, some aspects of the invention can have applications involving non-polymer samples. A non-polymer sample can be a material that comprises an organic or an inorganic non-polymer element or compound. For purposes herein, oligomers are considered to be polymers rather than non-polymers. The non-polymer molecule is, in some cases, preferably a non-biological non-polymer element or compound. Such non-biological non-polymer elements or compounds include non-polymer elements or compounds other than those having a well-characterized biological activity and/or a primary commercial application for a biological field (e.g., steroids, hormones, etc.). More particularly, such non-biological, non-polymer elements or compounds can include organic or inorganic pigments, carbon powders (e.g., carbon black), metals, metal compounds, metal oxides, metal salts, metal colloids, metal ligands, etc., without particular limitation. Other materials, which may be characterized according to the present invention include, without limitation, ceramic materials, semiconducting and conducting materials, metal and composites. Still other materials for which the present application finds untility are discussed elsewhere herein.

Sample Handling

Handling of sample materials may be accomplished with a plurality of steps which include withdrawing a sample from a sample container and delivering at least a portion of the withdrawn sample to a substrate. Handling may also include additional steps, particularly and preferably, sample preparation steps. In one approach, only one sample is withdrawn into a suitable liquid or solid dispensing device and only one sample resides in the probe at one time. In other embodiments, multiple samples may be drawn. In still other embodiments, multiple dispensers may be used in parallel.

In the general case, handling can be effected manually, in a semi-automatic manner or in an automatic manner. A sample can be withdrawn from a sample container manually, for example, with a pipette or with a syringe-type manual probe, and then manually delivered to a loading port or an injection port of a characterization system. In a semi-automatic protocol, some aspect of the protocol is effected automatically (e.g., delivery), but some other aspect requires manual intervention (e.g., withdrawal of samples from a process control line). Preferably, however, the sample(s) are withdrawn from a sample container and delivered to the characterization system in a fully automated manner—for example, with an auto-sampler.

In one embodiment, handling may be done using a microprocessor controlling an automated system (e.g., a robot arm). Preferably, the microprocessor is user-programmable to accommodate libraries of samples having varying arrangements of samples (e.g., square arrays with "n-rows" by "n-columns", rectangular arrays with "n-rows" by "m-columns", round arrays, triangular arrays with "r-" by "r-" by "r-" equilateral sides, triangular arrays with "r-base" by "s-" by "s-" isosceles sides, etc., where n, m, r, and s are integers).

Overview of Instruments and Methods

Figure 2A:
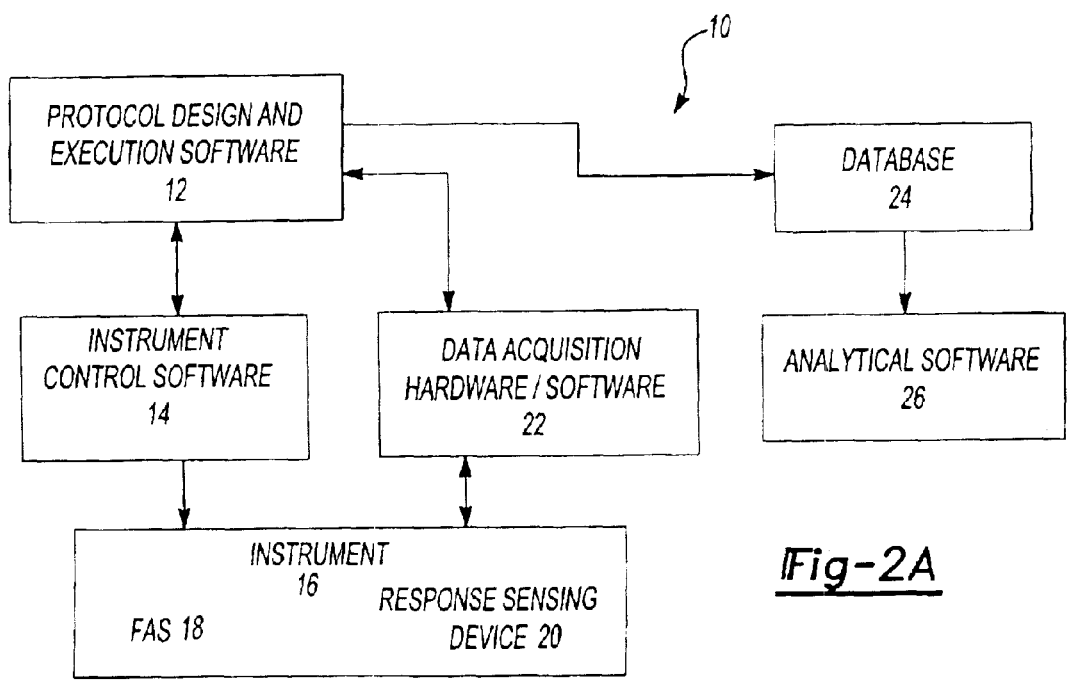
FIG. 2A shows a block diagram of a potential platform system for executing methods and for operating systems of the present invention.
Figure 2B:
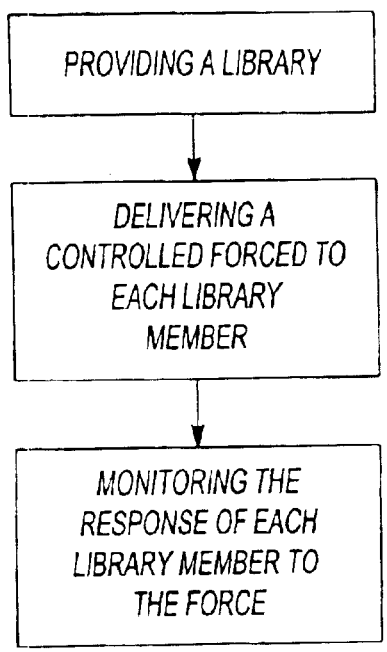
FIG. 2B shows a flowchart of the general steps for the methods of the present invention.

The present invention comprises instruments and methods for screening the mechanical or physical properties of a combinatorial library of materials by using at least one response sensing device to measure the responses of individual library members to forces applied by at least one force application source selected from the group consisting of a fluid, a voltage, a piezoelectric and a combination thereof (hereinafter known as "FAS"). Referring to FIGS. 2A–2B, there is a flow schematic diagram of an exemplary automated system 10 for parallel determination of mechanical properties of a library of materials 11 and a flowchart of the general steps for the methods of the present invention Generally, the system 10 includes a suitable protocol design and execution software 12 that can be programmed with information such as synthesis, composition, location information or other information related to the library 11 positioned with respect to a substrate or substrates. The protocol design and execution software 12 is typically in communication with instrument control software 14 for controlling the instrument 16 having at least one FAS 18 and at least one response sensing device 20. The protocol design and execution software 12 is also in communication with data acquisition hardware/software 22 for collecting data from response sensing device 20. Preferably, the instrument control software 14 commands the FAS 18 of the instrument 16 to apply force to each library member 11 in an effort to evoke a response from such library member 11. The actual displacement of each library member 11 by such force may be small (e.g., about 30 $\mu$m or less). At substantially the same time, the response sensing device 20 of the instrument 16 monitors the response of the library member 11, the force being applied to the library member 11 or both and provides data on the response to the data acquisition hardware/software 22. Thereafter, the instrument control software 14, the data acquisition hardware/software 22 or both transmit data to the protocol design and execution software 12 such that each library member 11 or information about each library member 11 may be matched with its response to the applied force and transmitted as data to a database 24. Once the data is collected in the database, analytical software 26 may be used to analyze the data, and more specifically, to determine mechanical properties of each library member 11, or the data may be analyzed manually.

In a preferred embodiment, the system 10 is driven by suitable software for designing the library, controlling the instruments for mechanical property screening, and data acquisition, viewing and searching, such as LIBRARY STUDIO™, by Symyx Technologies, Inc. (Santa Clara, Calif.); IMPRESSIONIST™, by Symyx Technologies, Inc. (Santa Clara, Calif.); EPOCH™, by Symyx Technologies, Inc. (Santa Clara, Calif.); or a combination thereof. The skilled artisan will appreciate that the above-listed software can be adapted for use in the present invention, taking into account the disclosures set forth in commonly-owned and copending U.S. patent application Ser. No. 09/174,856 filed on Oct. 19, 1998, U.S. patent application Ser. No. 09/305,830 filed on May 5, 1999 and WO 00/67086, U.S. patent application Ser. No. 09/420,334 filed on Oct. 18, 1999, U.S. application Ser. No. 09/550,549 filed on Apr. 14, 2000, each of which is hereby incorporated by reference. Additionally, the system may also use a database system developed by Symyx Technologies, Inc. to store and retrieve data with the overlays such as those disclosed in commonly-owned and copending U.S. patent application Ser. No. 09/755,623 filed on Jan. 5, 2001, which is hereby incorporated by reference for all purposes. The software preferably provides graphical user interfaces to permit users to design libraries of materials by permitting the input of data concerning the precise location on a substrate of a material (i.e., the address of the material). Upon entry, the software will execute commands to control movement of the robot, for controlling activity at such individual address. The versatile instruments and methods of the present invention can screen libraries of materials based on many different mechanical properties relating to Young's modulus (e.g., flexure, uniaxial extension, biaxial compression, and shear), failure (stress and strain at failure, toughness), adhesion, and others.

The instruments and methods of the present invention can conduct parallel, rapid-serial, serial-parallel and hybrid parallel-serial mechanical properties characterization. Some instruments and methods embodiments of the present invention are directed to parallel characterization of material samples, while others are directed to rapid serial or serial-parallel characterization of material samples. Throughout this specification, the specific preferred embodiments discussed in detail below are parallel embodiments. These particularly preferred embodiments have many detailed features, which may not be necessary in other embodiments of this invention. For example, less number of FAS and/or response sensing devices may be required in the rapid serial embodiments compared to the preferred parallel embodiments discussed below. Another example is that response sensing devices are placed remotely to the samples and are set at certain spacing in the preferred parallel embodiments discussed below. Those of skill in the art can easily modify such design parameters for other embodiments, such as by placing the response sensing devices at other spacing, not placing the response sensing devices substantially in a plane, etc. These are design choices for the present invention and describe other embodiments of the invention.

The several aspects of the characterization methods and systems disclosed and claimed herein can be advantageously employed separately, or in combination to efficiently characterize a variety of materials, with particular emphasis on polymeric materials. In preferred embodiments, these features are employed in combination to form a polymer characterization system that can operate as a high-throughput screen in a materials science research program directed to identifying and optimizing new materials, for instance, new polymers, new catalysts, new polymerization reaction conditions and/or new post-synthesis processing conditions. Certain characterizing information—particularly information obtainable from the present invention are broadly useful for characterizing polymers and polymerization reactions. As such, the particular materials and/or mechanisms disclosed herein should be considered exemplary of the invention and non-limiting as to the scope of the invention, which may be applicable in a variety of applications.

Bulge Test Instrument

Figure 4:
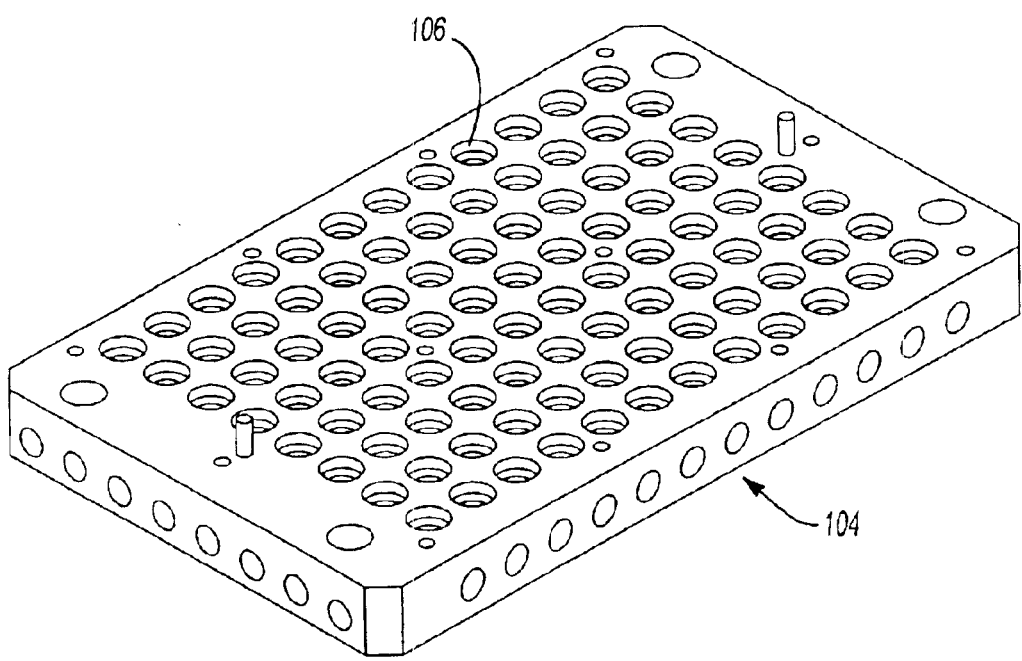
FIG. 4 shows a perspective view of one embodiment of a vessel that can be used in the bulge test instrument shown in FIG. 3.
Figure 3:
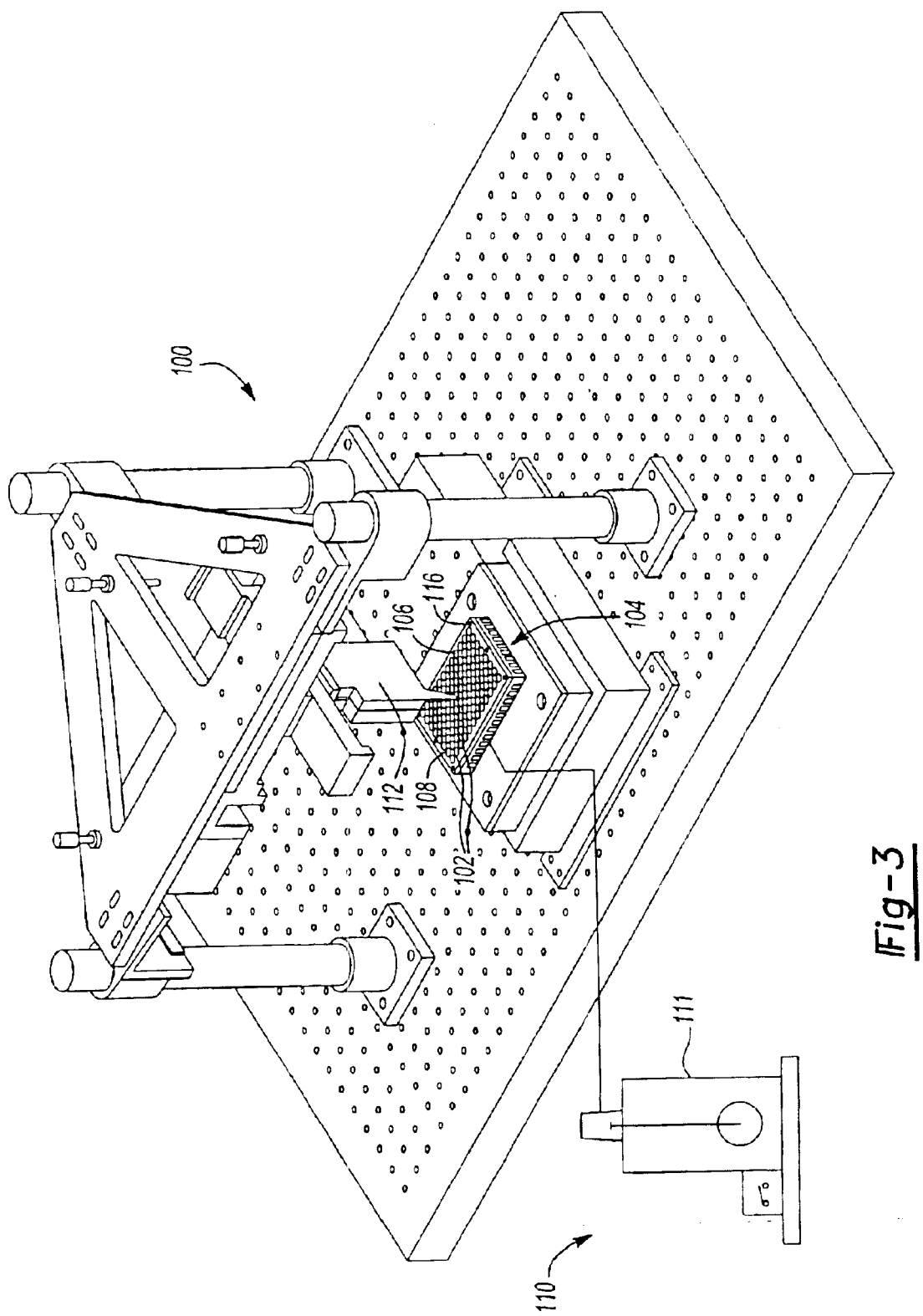
FIG. 3 shows a perspective view of one embodiment of a bulge test instrument that can be used for high throughput mechanical property screening.
Figure 5:
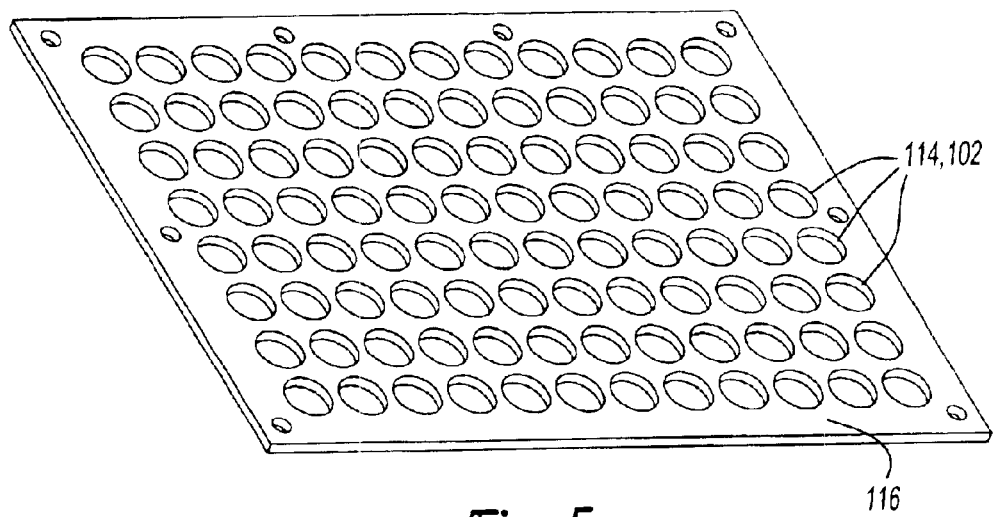
FIG. 5 shows a perspective view of one embodiment of a substrate that can be used in the bulge test instrument.

A bulge test instrument 100 is a preferred instrument of the present invention to measure mechanical properties of a library of materials 102. Referring to FIGS. 3–5, the instrument 100 is generally comprised of a mounting member that is adapted for defining a substantially gas-tight vessel 104, e.g., a block having a plurality of openings 106 to which the library of materials 102 is removably secured across the openings 106 for screening, at least one FAS 110 that is a pressure varying device 111 in combination with at least one fluid (not shown) that transmits the pressure (i.e., force) supplied by pressure varying device 111 to the library members 102, and at least one response sensing device 112 to measuring the response of each library member 102 to the forces delivered by the FAS 110. The vessel 104 can be constructed of any material, but it is preferably constructed of a sufficiently rigid material that the dimensions of the vessel do not change appreciably in response to changes in differential pressure. Examples of a preferred rigid material includes, without limitation, aluminum and stainless steel.

The securing of each library member 102 to the vessel 104 can be accomplished in any number of ways such as mechanically, magnetically, electromagnetically, electromechanically, chemically or a combination thereof. For example, the library member 102 can be secured across its respective opening by a mechanical clamp, an adhesive, or a combination of both. Referring to FIG. 5, the library of materials 102 is preferably placed on discrete and predefined regions 114 of a substrate or substrates 116. It is also preferred that the substrate is a flexible material. The predefined regions 114 generally correspond to unsecured or unclamped portions of the substrate(s) 116, which in FIG. 5, coincide with the openings 106 in the vessel 104. Useful substrate 116 materials include plastic sheets, such as a polyimide film, which may ranges in thickness on the order of from about 10 $\mu$m to about 100 $\mu$m. The library members 102 generally have comparable thickness, and preferably are about 20 $\mu$m thick. In some cases, clamping or fastening may be insufficient to secure the substrate(s) 116 to the vessel 104. Thus, in an alternative embodiment, the substrate(s) 116 may be bonded to the vessel 104 using a pressure sensitive adhesive. The adhesive should be less compliant than the substrate(s) 116, and during its application, care is taken to ensure a uniform bond line adjacent to the openings 106.

As discussed above, various methods can be used to make the library 102. For example, a library 102 comprised of polymers can be prepared by depositing known amounts of high viscosity fluid or solid materials 102 at the predefined regions 114 on substrate(s) 116. Following deposition, the library materials 102 and substrate(s) 116 are preferably compressed under melt-flow conditions to create polymer films of requisite thickness. Alternatively, the library members 102 can be dissolved in one or more solvents and deposited at the predefined regions 114 on the substrate(s) 116 using conventional liquid handling techniques such as automated pipetting. To prevent liquid library members 102 from spreading beyond their respective predefined regions 114, the substrate(s) 116 are pretreated—e.g., by selective etching or by silane treatment—to modify the surface energy of the substrate(s) 116 in or out of the predefined regions 114. See, for example, co-pending U.S. patent application entitled "Formation of Combinatorial Arrays of Materials Using Solution-Based Methodologies," Ser. No. 09/156,827, filed Sep. 18, 1998, and co-pending U.S. patent application, "Polymer Libraries on a Substrate, Method for Forming Polymer Libraries on a Substrate and Characterization Methods With Same," Ser. No. 09/567,598, filed May 10, 2000, each is herein incorporated by reference. Upon deposition, the liquid library members 102 are confined to predefined regions 114 having like surface energies, and form solid films following evaporation of the solvent. After brief annealing under vacuum to remove residual solvent, the thickness at the center or other location of each library member 102 can be measured using a variety of art disclosed techniques, including optical reflection profilometry, optical interference profilometry, or the like. In another embodiment, metallic, organometallic, or other compounds can be directly deposited on the substrate(s) 116 by chemical vapor deposition, physical vapor deposition, or similar art disclosed techniques.

In some instances, the size and placement of the library members 102 on the substrate(s) 116 can affect the measurements. Although thin films made by solution deposition techniques often have relatively uniform thickness near their centers, they exhibit substantial variation away from their centers, which can influence flexural measurements. To help minimize edge effects, library members 102 made by solution deposition techniques should generally extend beyond the regions defined by the openings 106.

The FAS 110 operates by having its pressure varying device 111 apply pressure to at least one library member 102 through a transmission fluid (i.e., gas or liquid). Examples of a pressure varying device 111 include, without limitation, a piston connected to the vessel 104 that varies the pressure within the vessel 104 by mechanical compression or expansion of a transmission fluid; a temperature controller for varying the temperature of a transmission fluid; a heat transfer device such as a resistance heater, a liquid-liquid heat exchanger that is connected to a reservoir of exchange fluid, a liquid-gas heat exchanger that is connected to a reservoir of exchange fluid, and a combination thereof. If a heat transfer device is used as the pressure varying device 111, then the region of transmission fluid that is heated or cooled is preferably separated from the region surrounding each library member 102 so as to minimize changes in the temperature of the library member 102. This is more easily achieved with gaseous transmission fluids, where the change in pressure within temperature is relatively large and the thermal conductivity of the medium is relatively low compared to liquid transmission fluids.

Pressure may be varied across more than one library member 102 simultaneously. This approach generally reduces the complexity of the instrument but may lead to a less robust instrument, as the mechanical failure of one secured library member 102 are likely to affect all other library members 102 that share the same FAS 110. Thus, it is preferred that each library member 102, secured across its respective opening 106 within the vessel 104, has its own FAS 110, response sensing device 112 or both. For clarity purpose, FIG. 3 only shows one response sensing device 112, but the present invention is not limited to having one response sensing device 112. For example, for some parallel embodiments, the instrument 100 may have numerous response sensing devices 112 up to, and even beyond, the number of members in the library 102. It is also acceptable to less number of response sensing devices 112 compared to the number of members in the library 102. Alternatively, the response sensing device 112 can be configured to translate in an x-y direction to measure the response of each library member 102 to the applied force one at a time in a rapid serial fashion.

The transmission fluid transmits the pressure variation generated by the pressure varying device 111 within the vessel 104 to its respective library member(s) 102. The transmission fluid is preferably chosen so as to be chemically inert with respect to the internal components of the vessel 104, and/or to the respective library member(s) 102. The compressibility of the transmission fluid is preferably chosen so that the means of varying the internal pressure is capable of generating pressure changes of the desired magnitude. Examples of a suitable transmission fluid include, without limitation, air, argon, hydrogen, nitrogen, helium, fluorocarbon liquids, ethanol, water, mercury, and mixture thereof. Fluorocarbon liquids, ethanol, and water are preferred transmission fluids for less compliant materials such as thin metal foils and mercury may be a suitable transmission fluid for extremely stiff material requiring extremely large pressure changes. In the event of a conflict between these requirements, two or more fluids may be used to transmit the pressure variation within the vessel 104. In this alternative preferred embodiment, the vessel 104 is designed such that one of the fluids remains in contact with its respective library member(s) 102 while the other fluid remains in contact with the pressure varying device 111, and both fluids are mutually immiscible. The separation of these fluids is preferred to be maintained through gravity, surface tension, or a mixture thereof.

The response (i.e., displacement) of each library member 102 to the pressure transmitted by the transmission fluid and applied by the pressure varying device 111 is measured by a response sensing device 112 as shown in FIG. 3. The response sensing device 112 can be a variety of commercially available electronic pressure sensors. Alternatively, the response sensing device 112 can measure the response optically, electrically, or via a dual pressure system.

Optical Response Sensing Devices

The response sensing device 112 can measure the response of each library member 102 to the force applied by the FAS 110 optically using art disclosed methods such as optical reflectance, optical interferometry, shadow illumination, and others. Examples of commercially available optical sensing devices 112 are Keyence Displacement Sensors Model Nos. LC-2450 and LC-2430 manufactured by Keyence Corporation (Woodcliff Lake, N.J.).

Optical reflectance generally involves illuminating the surface of each library member 102 by a highly collimated, monochromatic light source placed at a slight angle to the normal of the plane of the undeflected library member 102 and a detector aligned so as to detect the light scattered or reflected from the surface of the library member 102. Change in the height of the library member 102 produce changes in the signal received by the detector. Examples of a suitable light source include, without limitation, light emitting diodes (LEDs) and lasers. Examples of a suitable detector include, without limitation, a charge-coupled device (CCD), a photomultiplier, an avalanche photodiode, or an amplified photodiode.

Optical interferometry generally involves illuminating the surface of each library member 102 by a laser beam (monochromatic or polychromatic) with an incident beam directed along the normal to the plane of the undeflected library member by an optical train. The library member 102 and the end of the optical train define an optical cavity whose length is given by the distance from the end of the train to the surface of the library member 102. Some fraction of the incident beam is reflected from the surface of the library member 102, and the reflected and incident beams interfere. The optical train generally includes an element that splits the light reflected back from the surface of the library member 102 and directs part of the reflected light to a detector. Examples of a suitable optical train include, without limitation, appropriately aligned half-silvered mirrors, fiber optic beamsplitters, and the like. If a polychromatic light source is used, the split signal is then passed through or reflected from a diffraction grating (not shown) in order to separate the light into its spectral components. Examples of a suitable detector for both monochromatic and polychromatic light sources include, without limitation, a charge-coupled device (CCD), a photomultiplier, an avalanche photodiode, an amplified photodiode, and the like. For a monochromatic light source, variation in the optical train to the library member 102 distance generally produces a periodic variation in the intensity of the signal received at the detector. For a polychromatic light source, the signal receives by the detector displays a frequency-dependent oscillation in intensity which depends on the absolute value of the optical train to the library member distance.

Shadow illumination generally involves illuminating the surface of each library member 102 by a light source with an incident beam directed at an angle to the normal of the plane of the undeflected library member 102. The light reflected from the library member 102 and surrounding support is generally detected at a second, large angle with respect to the normal plane of the library member 102 by a detector. Examples of a suitable light source includes, without limitation, light-emitting diodes, conventional lamps, and the like. As the library member 102 is displaced by the pressure transmitted by the transmission fluid and applied by the FAS 110, some fraction of the reflected light is blocked by the library member 102, and some fraction of the light is reflected away from the detector. In one preferred embodiment, the detector measures the intensity of the light signal. Changes in this intensity are related to variation in the shape of the library member 102 as it is being deformed or displaced. Examples of a suitable detector for this embodiment include, without limitation, photodiodes and phototransistors. In another preferred embodiment, the detector is an imaging detector (e.g., a CCD) that records the shadow cast by the displaced library member and subsequent analysis may be performed to yield the shape of the library member.

Electrical Response Sensing Devices

The response sensing device 112 can measure the response of each library member to the force applied by the FAS 110 electrically using art disclosed methods such as capacitance, resistance, tunneling, electromechanical switching systems, or others.

One preferred capacitance method generally involves placing a commercial capacitive sensor in close proximity to the surface of each library member 102. The changes in the distance between the library member 102 and the capacitive sensor alter the combined capacitance of the capacitive sensor and the surrounding environment, resulting in a measurable voltage reading. An alternative capacitance method generally involves using a flexible and conductive material as the substrate(s) 116 (e.g., a piece of polyester coated with a thin layer of aluminum). The composite that is formed by each library member 102 and its respective substrate 116 is positioned in close proximity to a metal plate. The composite and the metal plate form a parallel plate capacitor in which the composite and the metal plate form the two electrodes. If the library member 102 is semiconducting or insulating, it behaves as a dielectric between the two plates of this capacitor. If the library member 102 is conducting, the electrical contact between the composite essentially makes the library sample 102 the first plate of the capacitor. Variation in the pressure across the composite produces changes in its shape that in turn lead to changes in the capacitance of the system. The changes in capacitance are detected by art disclosed techniques.

One preferred resistance method generally involves having a substrate 116 that exhibits changes in electrical resistance as a function of displacement. Examples of a suitable substrate 116 include, without limitation, polyimide, poly (ethylene terephthalate), a piezoresistive material, and the like. Measurements of the resistance of each library member 102 and its respective substrate 116 are preferably used to determine the displacement of the library member 102. In an alternative preferred embodiment, the substrate(s) 116 are diaphragm strain gages. Each diaphragm strain gage include two strain gages generally constructed out of two polyimide films enclosing a piezoresistive wire path made of stainless steel foil. Variations in the pressure across the substrate 116 lead to displacement of the substrate with its respective library member 102, which implies changes in the dimensions and resistance of the piezoresistive material.

The tunneling method generally involves having the substrate 116 with a conductive backing and a conducting electrode in the form of a sharp tip placed sufficiently close to the substrate 116 and its respective library member 102 so that when a known voltage is applied, electrons can tunnel from the tip to the substrate 116 or vice versa, depending on the sign of the voltage, resulting in a measurable current. This current depends exponentially on the tip and the substrate 116 separation, making this tunneling system a very sensitive technique for measuring displacement.

The electromechancial switching method generally involves having a mechanical contact between each displaced library member 102 and an art disclosed electromechanical assembly to complete or break a circuit path, thereby signaling that the displacement of the library member 102 has reached a particular value. The electromechanical assembly 112 is preferred engineered so that the forces resulting from this contact are negligible in comparison to those associated with displacement of the library member.

Dual Pressure Response Sensing Device

The dual pressure method generally involves securing each library member 102 between the vessel 104 and a second smaller vessel filled with a pressure transmission fluid and connected to a pressure sensor. The securing of each library member 102 between the two vessels can be accomplished in any number of ways such as mechanically, magnetically, electromagnetically, electromechanically, chemically or a combination thereof. Examples of suitable pressure transmission fluid and pressure sensor 126 are the same as described above. The displacement of the library member 102 is generally calculated based upon the volume enclosed by the second smaller vessel and the pressure measured by the pressure sensor.

Screening Using the Bulge Test Instrument

In a preferred method of the present invention for high throughput mechanical property screening, the library of materials 102 are removably secured across the openings 106 of the vessel 104 so part of each library member 102 is suspended over its respective opening 106. Force is then applied by the FAS 110 to the library through the FAS components—the pressure varying device 111 applying pressure to the transmission fluid, which transmits it to the library members 102. The applied pressure can vary (e.g., monotonically, sinusoidally, discontinuously or impulse like, etc.). The response (i.e., displacement) of each library member 102 to the pressure is monitored by its respective response sensing device 112 and used to determine the mechanical properties of the library member 102 based upon art disclosed analytical models. See, e.g., W. C. Young, *Roark's Formulas for Stress and Stain*, 1989; S. Timoshenko, *Theory of Plates and Shells*, McGraw-Hill, New York 1940. For example, when the pressure is applied across the library member 102 increases or decreases monotonically causing displacement of such library member 102, the displacement can be used to measure the flexure rigidity D of the library member 102 as shown here:

$$w = \frac{Pa^4}{64D}$$

where w is the library member's 102 center displacement, P is the applied pressure, and a is the library member's 102 radius. With the flexure rigidity value, the library member's Young's modulus E can also be measured:

$$E = \frac{12D(1-v^2)}{h^3}$$

where h is the library member's thickness and v is Poisson's ratio. Poisson's ratio may be the same for all members across the library 102 if they are all derived from the same or similar materials. Small variation in Poisson's ratio value across the library does not affect the result significantly as it is generally less than 0.5 and its square is much less than 1 (e.g., 0.3 for latexes). Once the Young's modulus of each library member 102 is known, other mechanical properties of the library member 102 such as uniaxial extension, biaxial compression, shear, glass transition temperature, melting point, toughness, stress and stain at failure, and others may also be derived using art disclosed techniques and analytical models. The mechanical properties that are preferably measured using the bulge test instrument 100 in accordance with the present invention include each library member's complex spectra of flexural rigidity and its complex spectra of Young's modulus within DC-1000 Hz frequency range and −100° C. to +200° C. temperature range.

Capacitive Pull-In Instrument

Figure 6:
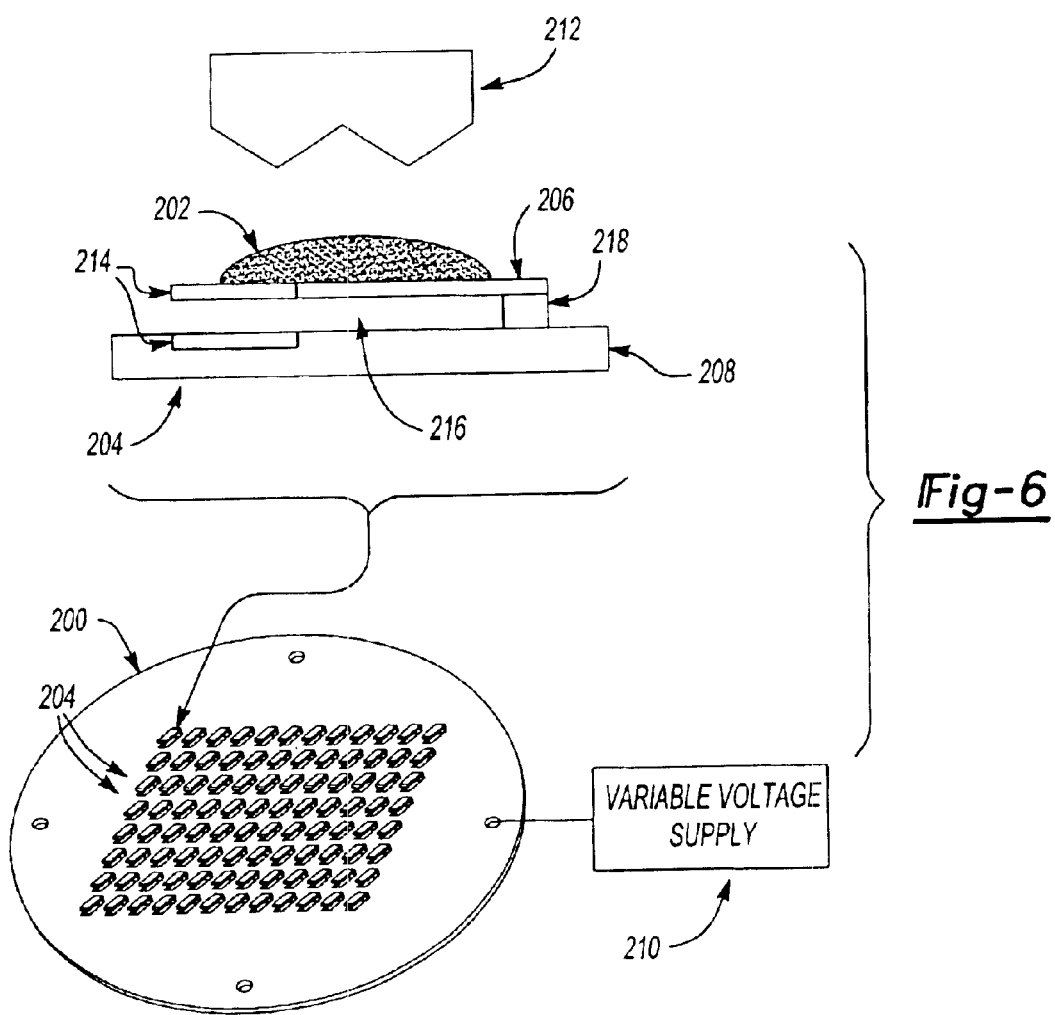
FIG. 6 shows a perspective view of one embodiment of a capacitive pull-in instrument that can be used for high throughput mechanical property screening.

A capacitive pull-in instrument 200 is a preferred instrument of the present invention to measure mechanical properties of a library of materials 202. Referring to FIG. 6, the capacitive pull-in instrument 200 is generally comprised of a plurality of capacitors 204 with each capacitor 204 having a first structure 206 and a second structure 208, wherein both structures (206, 208) are conductors of known Young's modulus and have dimensions that are electrically insulated from one another; at least one FAS 210; and at least one response sensing device 212. To help make the capacitive pull-in instrument more robust, it is preferred that each library member 202 has its own FAS 210 and/or response sensing device 212.

It is preferred that the first structure 206 and the second structures 208 are planar structures. However, structures of other shapes (e.g., circular, cured, bended, angular, or others) can also be used to form the two structures (206, 208). The structures (206, 208) preferably include a means of making electrical connections to each other in order to place a voltage across them. An example of such means of making electrical connections is metal contact points (e.g., electrodes) 214 placed on the structures (206, 208) by art disclosed techniques (e.g., vapor deposition). The structures (206, 208) are preferably separated from one another by at least one region 216, which may optionally be filled with a dielectric fluid (not shown). The structures (206, 208), in the absence of an applied voltage, are preferably maintained at a fixed distance by a suitable structure, force (e.g., magnetic) or the like 214. In a preferred embodiment, the structures (206, 208) are planar and they are maintained at a fixed distance by at least one spacer 218 attached to and positioned between them. The spacer 218 is preferably located at the edge of the structures (206, 208) so as to form a cantilever or other suspended structure, as shown in FIG. 6. Alternatively, the spacer 218 may be positioned at the center of the structures (206, 208). Another alternative is extending the spacer 218 around the perimeter of the structures (206, 208), which provides an additional advantage of preventing the individual library members from flowing or otherwise moving into the regions 216 between the structures (206, 208). Such overflow may prevent the desired occurrence of capacitive pull-in. The spacer 218 is preferably constructed of an insulating material (e.g., polyimide).

At least one FAS 210 varies the voltage applied to the capacitors 204. Examples of suitable FAS 210 include, without limitation, a variable voltage power supply, a combination of a programmable constant current source for charging the capacitor and a voltmeter for measuring the voltage difference across the capacitor, and the like. At least one response sensing device 212 is required to monitor the responses of the capacitors 204 and the library members 202 to the applied voltage. Examples of suitable response sensing devices 212 include, without limitation, the response sensing devices described above for the bulge test instrument 100 relating to optical reflectance, optical interferometry, shadow illumination, capacitance (using a high-frequency voltage signal superimposed on the DC voltage signal to measure the capacitance of the instrument 200), resistance (using a strain gage attached to one of the structures (206, 208), and electromechanical switching. Another preferred response sensing device 212 is to incorporate it into the structures (206, 208) by constructing one region on each of the planar structures from a semiconducting material (e.g., a wafer sensor). The region of the first structure 206 is p-doped and the region on the second structure 208 is n-doped or vice versa. Upon capacitive pull-in, these regions are brought into contact forming a diode across each of the capacitors 204 and resulting in a discontinuous drop in the voltage across each of the capacitors 204. For clarity purpose, FIG. 6 only shows one response sensing device 212, but the present invention is not limited to having one response sensing device 212. For example, for some parallel embodiments, the instrument 200 may have numerous response sensing devices 212 up to, and even beyond, the number of members in the library 202. It is also acceptable to less number of response sensing devices 112 compared to the number of members in the library 102. Alternatively, the response sensing device 212 can be configured to translate in an x-y direction to measure the response of each library member 202 to the applied force one at a time in a rapid serial fashion.

It is preferred that the plurality of capacitors 204 are assembled in a monolithic unit using semiconductor fabrication techniques in which they are made from a single wafer as shown in FIG. 6. In an alternative preferred embodiment, the plurality of capacitors 204 are assembled from physically separate components such as forming the structures (206, 208) from two separate wafers and the spacers 218 are produced by depositing insulating materials on selected regions of one or both wafers. An example of this alternative is using a disposable, flexible substrate such as polyimide on which metal has been deposited on one side in selected regions to produce a plurality of the first structures 206 and associated electrical contact points 210. The other side of this flexible substrate is coated with an adhesive to facilitate attachment to the spacers 218. To complete the plurality of capacitors 204, an identical flexible substrate, with selective deposition of metals or other conducting materials to act as electrical contact points 210, serves as the second planar structures 208 is also attached to the spacers 218. Alternatively, the second planar structures 208 may be constructed of a rigid material (e.g., silicon wafer) with appropriately positioned conducting and insulting regions. After the mechanical property screening, the flexible substrates forming the plurality of capacitors 204 may be removed from the instrument 200 and discarded, eliminating the need to clean the instrument 200 between screenings.

Screening Using the Capacitive Pull-In Instrument

In a preferred method of using the capacitive pull-in instrument 200 to measure mechanical properties of the library of materials 202, a voltage is applied by at least one FAS 210 across the capacitors 204 causing electric charges of opposite sign to accumulate on the planar structures (206, 208) resulting in applying one or more forces on each of them (206, 208). The one or more forces cause a displacement of the structures (208, 210), which increases the capacitance of the capacitors 204 resulting in a slight increase in the quantity of accumulated electrical charge on the structures (206, 208). The increase in the quantity of accumulated electrical charge on the structures (206, 208) again causes more force to be applied on each of the structures (206, 208) resulting in additional displacement. The displacements can be expressed, for instance, as a geometric series. The voltage applied by the at least one FAS 210 can be non-oscillatory or oscillatory. For low voltages, the series typically converges to a finite value, which is considerably less than the separation of the structures (206, 208), and the instrument 200 is mechanically stable. However, for high voltages, the series may not converge, and the capacitors 204 become mechanically unstable causing the structures (206, 208) to draw together. The voltage at which this instability occurs (i.e., the pull-in voltage) depends on the shape and mechanical properties of the structures (206, 208). Accordingly, using art disclosed analytical models, a measurement of the pull-in voltage can be used to extract the mechanical properties of the structures (206, 208) in the absence of any library member 202. See, e.g., P. M. Osterberg and S. D. Senturia, "M-TEST: A Test Chip for MEMS Material Property Measurement Using Electrostatically Actuated Test Structures," *Journal of Microelectromechanical Systems*, Vol. 6, No. 2, June 1997 and is incorporated herein by reference. Thereafter, the library members are individually secured onto the first structures 206 as shown in FIG. 6. The securing of each library member 202 to its respective first structure 206 can be accomplished in any number of ways such as mechanically, magnetically, electromagnetically, electromechanically, chemically or a combination thereof. A voltage is again applied by at least one FAS 210 across the capacitors 204, the resulting pull-in voltage is measured again, and the ratio between the library 202 present and the library 202 absent values is determined and Young's modulus of each library member 202 can be calculated using art disclosed analytic models. Once the Young's modulus of each library member 202 is known, other mechanical properties of the library member 202 such as flexure, uniaxial extension, biaxial compression, shear, glass transition temperature, melting point, toughness, stress and stain at failure, adhesion, and the like may also be derived using art disclosed techniques and analytical models. The mechanical properties that are preferably measured using the capacitive pull-in instrument 200 in accordance with the present invention include each library member's complex spectra of flexural rigidity and its complex spectra of Young's modulus within DC-1000 Hz frequency range and −100° C. to +200° C. temperature range.

Piezoelectric Instrument

Figure 7:
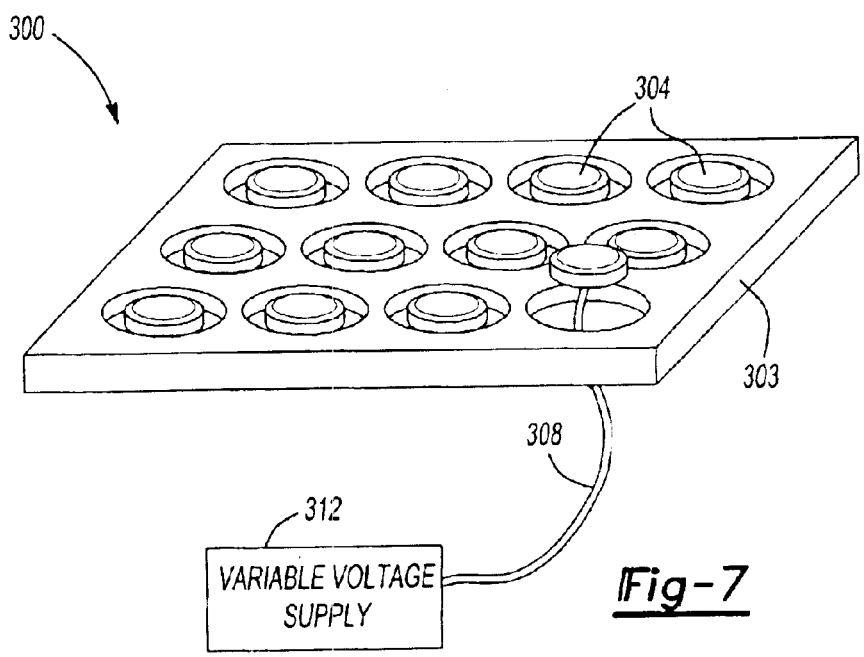
FIG. 7 shows a perspective view of one embodiment of a piezoelectric instrument that can be used for high throughput mechanical property screening.
Figure 8:
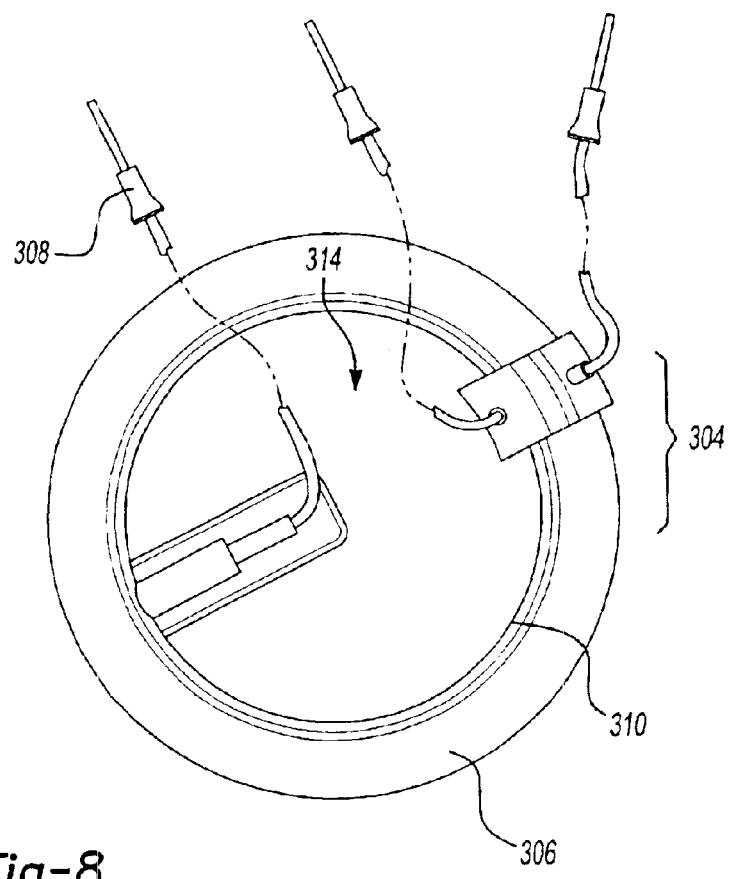
FIG. 8 shows a view of one end of an embodiment of a piezoelectric bender that can be used in the piezoelectric instrument shown in FIG. 7.

A piezoelectric instrument 300 is a preferred instrument of the present invention to measure mechanical properties of a library of materials 302. Referring to FIGS. 7–9, the piezoelectric instrument 300 is generally comprised of a supporting frame 303 containing a plurality of piezoelectric benders 304 (illustrated as disk benders), each having a backing plate 306, an electrode 308, and an appropriately polarized ceramic disk 310; at least one FAS 312 that is preferably a variable voltage supply source; and at least one response sensing device 314. The backing plate 306 is preferably constructed out of a metal, more preferably, brass or stainless steel. The electrode 308 is preferably sintered, glued, fastened, or otherwise joined to the backing plate 306.

The library members 302 are secured to the backing plates 306. The securing of each library member 302 to its respective backing plate 306 can be accomplished in any number of ways such as mechanically, magnetically, electromagnetically, electromechanically, chemically or a combination thereof. It is preferred that the library members 302 are directly deposited onto the backing plates 306. Alternatively, a thin layer of coupling liquid can be used to secure the library members 302 to the backing plates 306.

Voltage is applied to each library member 302 via the voltage supply source 312 to the electrode 308 triggering a change in the diameter of the ceramic disk 310 and thereby causing the entire bender 304 to buckle as shown in FIG. 10. Referring to FIG. 8, small part of the electrode 308 on the bender 304 can be separate out so that the stress field in the ceramic disk 310 is not considerably disturbed. This electrode 308 and a part of the bender 304 underneath can be used as the response sensing device 314. Other suitable response sensing devices 314 include, without limitation, the optical response sensing devices described above for the bulge test instrument 100 relating to optical reflectance, optical interferometry, and shadow illumination. For clarity purpose, FIG. 7 only shows one response sensing device 314, but the present invention is not limited to having one response sensing device 314. For example, for some parallel embodiments, the piezoelectric instrument 300 may have numerous response sensing devices 314 up to, and even beyond, the number of members in the library 302. Alternatively, the response sensing device 314 can be configured to translate in an x-y direction to measure the response of each library member 302 to the applied force one at a time in a rapid serial fashion. To make the piezoelectric instrument 300 more robust, it is preferred that each library member 302 has its own voltage supply source 312 and response sensing device 314.

In an alternative preferred embodiment of the piezoelectric instrument 300, the benders 304 are replaced a plurality of piezoelectric elements each having with a sensor region and an actuator region. Alternatively, each piezoelectric element can be replaced by a separate piezoelectric sensor element and a separate piezoelectric actuator element connected to each other by a platform.

Screening Using the Piezoelectric Instrument

In a preferred method of using the piezoelectric instrument 300 to measure mechanical properties of the library of materials, a voltage, preferably sinusoidally, is applied by at least one variable voltage supply source 312 to the benders 304 causing their ceramic disks 310 to generate a stress field across each library member 302. The resulting strain in each library member 302 is measured by its respective response sensing device 314. Using art disclosed analytic models, the Young's modulus of each bender 304, without the library present, is obtained. Thereafter, the library members 302 are secured onto the backing plates 306 of the benders 304 and another voltage is applied by the at least one variable voltage supply source 312 at variable frequency to the benders 304 resulting in the application of sinusoidal pressure to the library 302 and the benders 304. Voltage across the response sensing devices 314 is proportional to each library member's displacement and can be used to calculate the Young's modulus of each library member 302 based upon art disclosed analytical models. Once the Young's modulus of each library member 302 is known, other mechanical properties of the library member 202 such as flexure, uniaxial extension, biaxial compression, shear, glass transition temperature, melting point, toughness, stress and stain at failure, or others may also be derived using art disclosed techniques and analytical models. The mechanical properties that are preferably measured using the piezoelectric instrument 300 in accordance with the present invention include each library member's complex spectra of flexural rigidity and its complex spectra of Young's modulus within DC-1000 Hz frequency range and −100° C. to +200° C. temperature range.

Environmental Control Device

Figure 11:
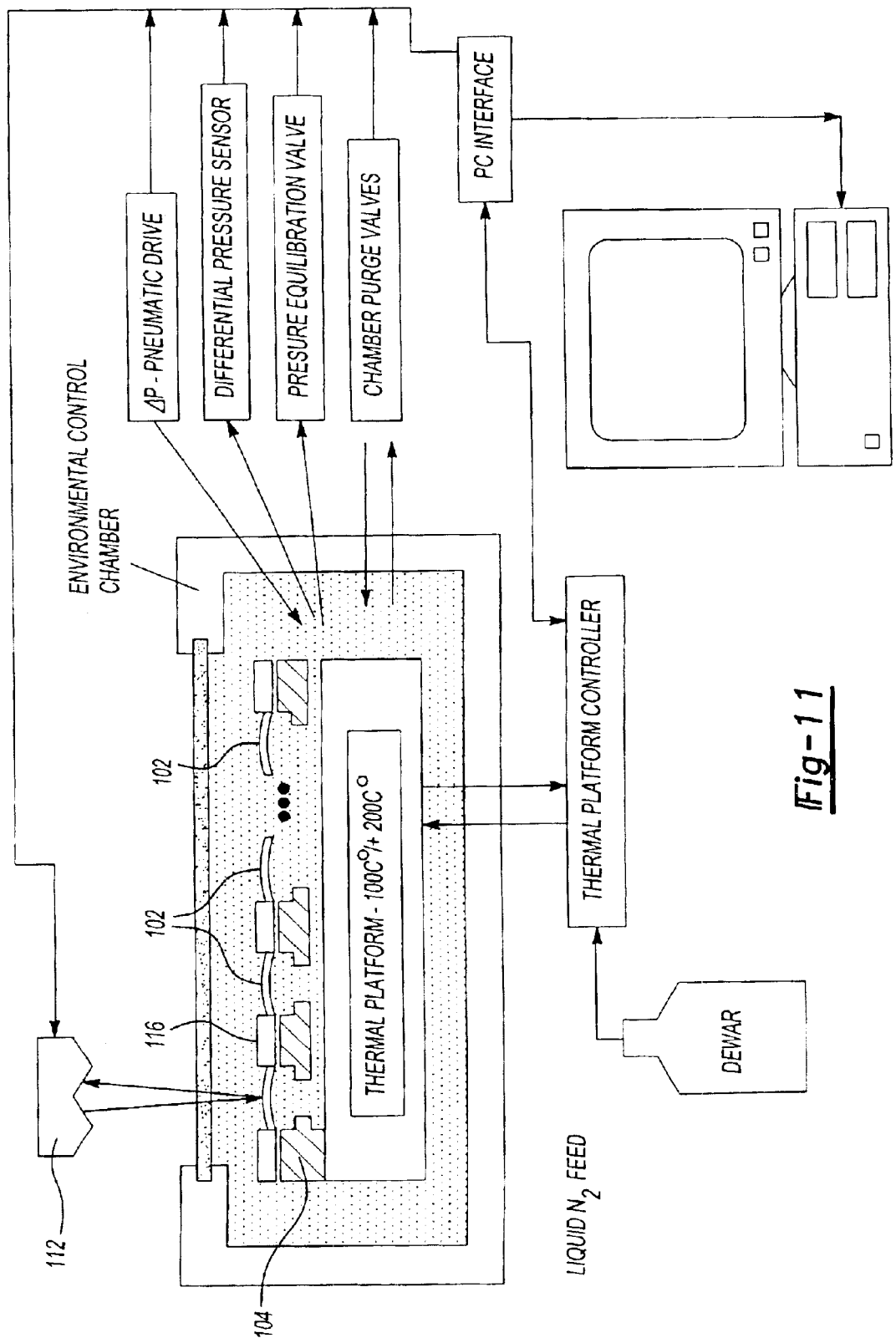
FIG. 11 shows a schematic view of one embodiment of a bulge test instrument with an environmental chamber.

Since the mechanical properties of materials can depend strongly on environmental conditions—temperature, pressure, ambient gas composition (including humidity), electric and magnetic field strength, and so on—the screening instruments discussed above may include a control system for regulating environmental conditions as shown in FIG. 11. Useful control systems include an environmental chamber that encloses the sample, the sample holder, and the FAS. The system may also uses computer software to regulate conditions in the environmental chamber. As discussed below, the system may locate the response sensing device outside of the environmental chamber if their performance is strongly influenced by any of the environmental control variables, such as temperature. Measurements may be performed as a function of the value of one or more of these quantities, or may be performed as a function of time elapsed after a change in the value of one or more of these quantities. The means by which these changes may be produced are described in detailed in the commonly owned U.S. Pat. No. 6,157,449 and U.S. patent application Ser. No. 09/579,338 titled "Rheo-Optical indexer and Method of Screening and Characterizing Arrays of Materials", filed on May 25, 2000 (Carlson, et al.), which is incorporated herein by reference for all purposes.

Screening Throughput

The instruments described above in accordance with the present invention can screen a library having 2 or more material samples, and preferably, at least 8 samples to ensure adequate screening throughput. Those of skill in the art will appreciate that lower or higher throughput may serve the needs of a particular application of this invention. Thus, 4 or more, 8 or more, 16 or more, 24 or more, or 48 or more FAS and/or response sensing devices in parallel are within the scope of this invention.

For methods directed to characterizing a plurality of samples, a property of each of the samples or of one or more components thereof is detected—serially or in a parallel, serial-parallel or hybrid parallel-serial manner—at an average sample throughput of not more than about 10 minutes per sample. As used in connection herewith, the term "average sample throughput" refers to the sample-number normalized total (cumulative) period of time required to detect a property of two or more samples with a characterization system. The total, cumulative time period is delineated from the initiation of the characterization process for the first sample, to the detection of a property of the last sample or of a component thereof, and includes any intervening between-sample pauses in the process. The sample throughput is more preferably not more than about 8 minutes per sample, even more preferably not more than about 4 minutes per sample and still more preferably not more than about 2 minutes per sample. Depending on the quality resolution of the characterizing information required, the average sample throughput can be not more than about 1 minute per sample, and if desired, not more than about 30 seconds per sample, not more than about 20 seconds per sample or not more than about 10 seconds per sample, and in some applications, not more than about 5 seconds per sample and not more than about 1 second per sample. Sample-throughput values of less than 4 minutes, less than 2 minutes, less than 1 minute, less than 30 seconds, less than 20 seconds and less than 10 seconds are demonstrated in the examples. The average sample-throughput preferably ranges from about 10 minutes per sample to about 10 seconds per sample, more preferably from about 8 minutes per sample to about 10 seconds per sample, even more preferably from about 4 minutes per sample to about 10 seconds per sample and, in some applications, most preferably from about 2 minutes per sample to about 10 seconds per sample.

As for screening throughput for parallel embodiments, up to 96 library members may have their mechanical properties measured simultaneously in about 10 minutes or less, preferably about 5 minutes or less and even more preferably in about 1 minute or less. In some parallel embodiments, screening throughput of even about 30 seconds or less may be accomplished for an array of the sizes discussed herein, e.g., up to 96 samples or members in the array.

A sample-throughput of 10 minutes per sample or less is important for a number of reasons. Systems that detect a property of a sample or of a component thereof at the aforementioned sample throughput rates can be employed effectively in a combinatorial research program. From a completely practical point of view, the characterization rates are also roughly commensurate with reasonably-scaled polymer sample library synthesis rates. It is generally desirable that combinatorial screening systems, such as the polymer characterization protocols disclosed herein, operate with roughly the same sample throughput as combinatorial synthesis protocols—to prevent a backlog of uncharacterized polymerization product samples. Hence, because moderate scale polymer-synthesis systems, such as the Discovery Tools™ PPR-48™ (Symyx Technologies, Santa Clara Calif.), can readily prepare polymer libraries with a sample-throughput of about 100 polymer samples per day, a screening throughput of about 10 minutes per sample or faster is desirable. Higher throughput synthesis systems demand higher characterization throughputs. The preferred higher throughput values are also important with respect to process control applications, to provide near-real time control data.

Additionally, as shown in connection with the examples provided herein, the characterization of polymer samples at such throughputs can offer sufficiently rigorous quality of data, to be useful for scientifically meaningful exploration of the material compositional and/or reaction conditions research space.

Other Screens

The present invention may be employed by itself or in combination with other screening protocols for the analysis of liquids or their consitituents. Without limitation, examples of such screening techniques include those addressed in commonly-owned U.S. Pat. Nos. 6,182,499 (McFarland, et al); 6,175,409 B1 (Nielsen, et al); 6,157,449 (Hajduk, et al); 6,151,123 (Nielsen); 6,034,775 (McFarland, et al); 5,959,297 (Weinberg, et al), 5,776,359 (Schultz, et al.), commonly owned and co-pending U.S. patent application Ser. No. 09/580,024 titled "Instrument for High Throughput Measurement of Material Physical Properties and Method of Using Same," filed on May 26, 2000, all of which are hereby expressly incorporated by reference herein.

Screening techniques may also include (without limitation) optical screening, infrared screening, electrochemical screening, flow characterization (e.g., gas, liquid or gel-phase chromatography), spectrometry, crystallography, or the like.

It will be appreciated from the above that many alternative embodiments exist for high throughput mechanical property screening within the scope of the present invention. Accordingly, the instruments and methods discussed above are to be considered exemplary and nonlimiting as to the scope of the invention.

What is claimed is:

1. A method for screening an array of materials for a mechanical property, comprising:

providing a flexible substrate;

depositing a library comprising at least four different material samples onto said substrate;

mounting said substrate onto a mounting member with at least four openings, such that said at least four samples are at least partially aligned with said at least four openings;

applying pressure with at least one fluid to cause each of said samples to displace in response to said pressure; and monitoring a response of each of said samples to said pressure with at least one response sensing device.

2. The method of claim 1, wherein the method is capable of screening at least two of said samples of said library simultaneously.

3. The method of claim 1, wherein the method is capable of screening at least twenty-four samples of said library simultaneously.

4. The method of claim 1, wherein a screening throughput rate of said library is no greater than about ten minutes.

5. The method of claim 1, wherein said pressure is applied to each of said samples in sequential order and a screening throughput rate is no greater than 10 minutes per said sample.

6. The method of claim 1, wherein said mechanical property is selected from the group consisting of flexure, uniaxial extension, biaxial compression, shear, stress and strain at failure, toughness, storage modulus, loss modulus, and mixtures thereof.

7. The method of claim 1, further comprising regulating environmental conditions of said samples.

8. The method of claim 1, wherein said at least one response sensing device is selected from the group consisting of an electronic pressure sensor, an optical response sensing device selected from the group consisting of optical reflectance, optical interferometry, shadow illumination, and a combination thereof, an electrical response sensing device selected from the group consisting of capacitance, resistance, tunneling, electromechanical switching, and a combination thereof, a dual pressure sensing device, and a combination thereof.

9. The method of claim 1, wherein said samples are mounted on said substrates by mechanically securing, magnetically securing, electromagnetically securing, electromechanically securing, chemically securing, or a combination thereof.

10. The method of claim 1, wherein said pressure applied by said fluid is created by a source selected from the group consisting of a piston in a cylinder, a temperature controller for varying the temperature of said fluid, a heat transfer device selected from the group consisting of a resistance heater, a liquid-liquid heat exchanger that is connected to a reservoir of exchange fluid, a liquid-gas heat exchanger that is connected to a reservoir of exchange fluid and a combination thereof, and a combination thereof.

11. The method of claim 1, wherein said fluid is chemically inert to said library of material samples, allows said pressure applied to said samples to be controlled and variable, and is selected from the group consisting of air, argon, hydrogen, nitrogen, helium, fluorocarbon liquids, ethanol, water, mercury and mixtures thereof.

12. The method of claim 1, wherein at least two fluids are used to apply pressure to one of said samples, said two fluids being mutually immiscible and wherein separation between said two fluids is maintained by gravity, surface tension, or a mixture thereof.

13. The method of claim 1, wherein said pressure is a negative pressure.

14. The method of claim 1, wherein each of said samples has an area of less than about 100 mm$^2$.

15. The method of claim 1, wherein each of said sample has a thickness of less than about 500 microns.

16. The method of claim 1, wherein said pressure is selected from the group consisting of monotonic, sinusoidal, discontinuous, and a combination thereof.

17. A method for screening an array of materials for a mechanical property, comprising:
providing a flexible substrate;
depositing a library of at least four different material samples onto said substrate;
measuring the thickness of each of said samples;
mounting said substrate onto a mounting member with at least four openings, such that said at least four samples are at least partially aligned with said at least four openings;
compressing at least one transmission fluid against said substrate causing a pressure to be applied to each of said samples;
monitoring a response of each of said samples to said compression with at least one response sensing device selected from a the group consisting of an electronic pressure sensor, an optical response sensing device, an electrical response sensing device, a dual pressure sensing device, and a combination thereof; and
ranking said samples relative to each other according to their respective performance.

18. The method of claim 17, wherein the method is capable of screening at least two of said samples of said library simultaneously.

19. The method of claim 17, wherein a screening throughput rate of said library is no greater than about ten minutes.

20. The method of claim 17, wherein said pressure is applied to each of said samples in sequential order and a screening throughput rate is no greater than 10 minutes per said sample.

21. The method of claim 17, wherein said mechanical property is selected from the group consisting of flexure, uniaxial extension, biaxial compression, shear, stress and strain at failure, toughness, Young's modulus, complex modulus, and mixtures thereof.

22. The method of claim 17 further comprising regulating environmental conditions of said samples.

23. The method of claim 17, wherein said samples are mounted on said substrates by mechanically securing, magnetically securing, electromagnetically securing, electromechanically securing, chemically securing, or a combination thereof.

24. The method of claim 17, wherein said compression originates from a source selected from the group consisting of a piston in a cylinder, a temperature controller for varying the temperature of said transmission fluid, a heat transfer device selected from the group consisting of a resistance heater, a liquid-liquid heat exchanger that is connected to a reservoir of exchange fluid, a liquid-gas heat exchanger that is connected to a reservoir of exchange fluid and a combination thereof, and a combination thereof.

25. The method of claim 17, wherein said transmission fluid is chemically inert to said samples, allows said compression to be controlled and variable, and is selected from the group consisting of air, argon, hydrogen, nitrogen, helium, fluorocarbon liquids, ethanol, water, mercury and mixtures thereof.

26. The method of claim 17, wherein two transmission fluids are used to apply pressure to one of said samples, wherein said two transmission fluids are mutually immiscible and separation between said two transmission fluids is maintained by gravity, surface tension, or a mixture hereof.

27. The method of claim 17, wherein each of said samples has an area of less than about 100 mm$^2$.

28. The method of claim 17 wherein each of said samples has a thickness of less than about 500 microns.

29. A method for screening an array of materials for a mechanical property, comprising:
providing a mounting member having a plurality of openings, wherein said mounting member is adapted for connection to a source of a fluid pressure;
placing a flexible substrate having a library of at least two different material samples deposited thereon onto a surface of said mounting member over said openings for defining a substantially gas tight vessel, wherein each of said samples has an area of less than about 100 mm$^2$ and a thickness of less than 500 microns;
aligning said samples with said openings;
introducing at least one fluid that is chemically inert to said samples, and is selected from a the group consisting of air, argon, hydrogen, nitrogen, helium, fluorocarbon liquids, ethanol, water, mercury and mixtures thereof into said mounting member for applying pressure to each of said samples;
regulating environmental conditions of said samples;
using a source selected from the group consisting of a piston in a cylinder, a temperature controller for varying the temperature of said transmission fluid, a heat transfer device selected from the group consisting of a resistance heater, a liquid-liquid heat exchanger that is connected to a reservoir of exchange fluid, a liquid-gas heat exchanger that is connected to a reservoir of exchange fluid and a combination thereof, and a combination thereof, to apply pressure to said substrate and causing each of said samples to displace in response to said pressure; and monitoring a response of each of said samples to said pressure with at least one response sensing device selected from the group consisting of an electronic pressure sensor, an optical response sensing device, an electrical response sensing device, a dual pressure sensing device, and a combination thereof, wherein said mechanical property is selected from the group consisting of flexure, uniaxial extension, biaxial compression, shear, stress and strain at failure, toughness, Young's modulus, complex modulus, and mixtures thereof.

30. The method of claim 29, wherein the method is capable of screening at least two of said samples of said library simultaneously.

31. The method of claim 29, wherein a screening throughput rate of said library is no greater than about ten minutes.

32. The method of claim 29, wherein said pressure is applied to each of said samples in sequential order and a screening throughput rate is no greater than 10 minutes per said sample.

33. The method of claim 29, wherein two fluids are used to apply pressure to one of said samples, wherein said two fluids are mutually immiscible and separation between said two fluids is maintained by gravity, surface tension, or a mixture thereof.

* * * * *

UNITED STATES PATENT AND TRADEMARK OFFICE
CERTIFICATE OF CORRECTION

PATENT NO. : 6,772,642 B2  Page 1 of 1
APPLICATION NO. : 09/939404
DATED : August 10, 2004
INVENTOR(S) : Hajduk et al.

It is certified that error appears in the above-identified patent and that said Letters Patent is hereby corrected as shown below:

Col. 29, line 38, delete "sample" and insert --samples--
Col. 29, line 59, delete the word "a" between "from" and "the"
Col. 30, line 38, delete "hereof" and insert --thereof--
Col. 30, line 57, delete the word "a" between "from" and "the"

Signed and Sealed this

Eighth Day of January, 2008

JON W. DUDAS
*Director of the United States Patent and Trademark Office*